United States Patent
Ramamurthy et al.

(10) Patent No.: US 10,975,313 B2
(45) Date of Patent: *Apr. 13, 2021

(54) CONVERSION OF WASTE PLASTIC THROUGH PYROLYSIS TO HIGH VALUE PRODUCTS LIKE BENZENE AND XYLENES

(71) Applicant: SABIC Global Technologies B.V., Bergen op Zoom (NL)

(72) Inventors: Krishna Kumar Ramamurthy, Bengaluru (IN); Ravichander Narayanaswamy, Bengaluru (IN); Venkata Ramanarayanan Ganapathy Bhotla, Bangalore (IN); Alexander Stanislaus, Bangalore (IN); Santosh Ganji, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 13 days.

This patent is subject to a terminal disclaimer.

(21) Appl. No.: 16/468,071

(22) PCT Filed: Jan. 3, 2018

(86) PCT No.: PCT/IB2018/050043
§ 371 (c)(1),
(2) Date: Jun. 10, 2019

(87) PCT Pub. No.: WO2018/127812
PCT Pub. Date: Jul. 12, 2018

(65) Prior Publication Data
US 2020/0017773 A1 Jan. 16, 2020

Related U.S. Application Data

(60) Provisional application No. 62/442,684, filed on Jan. 5, 2017.

(51) Int. Cl.
*C10G 1/10* (2006.01)
*C07C 2/66* (2006.01)
(Continued)

(52) U.S. Cl.
CPC ............ *C10G 1/10* (2013.01); *B01J 6/008* (2013.01); *B01J 19/245* (2013.01);
(Continued)

(58) Field of Classification Search
None
See application file for complete search history.

(56) References Cited

U.S. PATENT DOCUMENTS 3,901,951 A  8/1975  Nishizaki ............ 260/669 R
4,162,214 A  7/1979  Maslyansky et al. ...... 585/471
(Continued)

FOREIGN PATENT DOCUMENTS

CN  105358509 A  2/1916
CN  103880584 A  6/2014
(Continued)

OTHER PUBLICATIONS

International Search Report and Written Opinion from PCT/IB2018/050043 dated May 2, 2018, 10 pages.
(Continued)

*Primary Examiner* — Philip Y Louie
(74) *Attorney, Agent, or Firm* — Norton Rose Fulbright US LLP

(57) ABSTRACT

A process for producing benzene and xylenes comprising introducing hydrocarbon liquid stream to hydroprocessor to yield first gas stream and hydrocarbon product ($C_5+$); optionally introducing hydrocarbon product to first aromatics separating unit to produce saturated hydrocarbons ($C_5+$) and first aromatics stream ($C_6+$); feeding hydrocarbon product and/or saturated hydrocarbons to reformer to produce
(Continued)

reformer product, second gas stream, and hydrogen stream; introducing reformer product to second aromatics separating unit to produce a non-aromatics recycle stream and second aromatics stream comprising $C_6+$ aromatics; recycling non-aromatics recycle stream to reformer; introducing first aromatics stream and/or second aromatics stream to third aromatics separating unit to produce first $C_6$ aromatics (benzene), $C_7$ aromatics (toluene), $C_8$ aromatics (xylenesðylbenzene), $C_9$ aromatics, $C_{10}$ aromatics, and $C_{11}+$ aromatics; introducing $C_7$ aromatics, $C_9$ aromatics, $C_{10}$ aromatics, or combinations thereof to disproportionation and transalkylation unit to yield third aromatics stream (benzene and xylenes); and conveying $C_{11}+$ aromatics to hydroprocessor.

19 Claims, 3 Drawing Sheets

(51) Int. Cl.
| | | |
|---|---|---|
| *C07C 6/04* | (2006.01) | |
| *C07C 6/10* | (2006.01) | |
| *B01J 6/00* | (2006.01) | |
| *B01J 19/24* | (2006.01) | |
| *B09B 3/00* | (2006.01) | |
| *C07C 5/27* | (2006.01) | |
| *C07C 6/12* | (2006.01) | |
| *C10B 53/07* | (2006.01) | |
| *C10G 1/00* | (2006.01) | |
| *C10G 69/04* | (2006.01) | |

(52) U.S. Cl.
CPC ............. *B09B 3/0083* (2013.01); *C07C 2/66* (2013.01); *C07C 5/277* (2013.01); *C07C 6/123* (2013.01); *C10B 53/07* (2013.01); *C10G 1/002* (2013.01); *C10G 69/04* (2013.01); *C10G 2300/1003* (2013.01); *C10G 2300/42* (2013.01); *C10G 2400/30* (2013.01)

(56) References Cited

U.S. PATENT DOCUMENTS

| | | | |
|---|---|---|---|
| 4,746,406 A | 5/1988 | Timmann | 201/25 |
| 9,249,068 B2 | 2/2016 | Tinger et al. | |
| 2009/0227823 A1 | 9/2009 | Huber et al. | 585/324 |
| 2014/0121426 A1 | 5/2014 | Tandon | 585/241 |
| 2015/0038755 A1* | 2/2015 | Corradi | C10G 29/205 585/470 |
| 2015/0166435 A1* | 6/2015 | Serban | C10G 63/08 585/321 |
| 2015/0321976 A1 | 11/2015 | Larson et al. | |
| 2015/0376086 A1 | 12/2015 | Tinger et al. | |

FOREIGN PATENT DOCUMENTS

| | | |
|---|---|---|
| EP | 2956525 A1 | 12/2015 |
| IN | 676DEL2010 | 12/2012 |
| WO | WO2016009333 A1 | 1/2016 |

OTHER PUBLICATIONS

Kaminsky et al. "Pyrolysis of mixed plastics into aromatics." Journal of Analytical and Applied Pyrolysis, vol. 51, Issues 1-2, Jul. 1999, pp. 127-134.

Kaminsky et al. "Thermal degradation of mixed plastic waste to aromatics and gas." Polymer Degradation and Stability, vol. 53, Issue 2, Aug. 1996, pp. 189-197.

* cited by examiner

CONVERSION OF WASTE PLASTIC THROUGH PYROLYSIS TO HIGH VALUE PRODUCTS LIKE BENZENE AND XYLENES

This application is a national phase application under 35 U.S.C. § 371 of International Application No. PCT/IB2018/050043 filed Jan. 3, 2018, which claims priority to U.S. Provisional Patent Application No. 62/442,684 filed Jan. 5, 2017. The entire contents of each of the above-referenced disclosures is specifically incorporated by reference herein without disclaimer.

TECHNICAL FIELD

This disclosure relates to the production of aromatic hydrocarbons from mixed plastics via processes which include pyrolysis, hydroprocessing, reforming, and disproportionation and alkylation, wherein benzene and xylenes are the preferred products.

BACKGROUND

Benzene and xylenes are important chemicals, with applications ranging from chemical intermediates to solvents. Benzene is a natural constituent of crude oil and it is used primarily as a precursor for manufacturing chemicals with more complex structure, such as ethylbenzene, cumene, cyclohexane, nitrobenzene, and alkylbenzenes. Benzene also has a high octane number, and as such is an important component of gasoline. Benzene can also be used for making some types of rubbers, lubricants, dyes, detergents, drugs, explosives, and pesticides.

While xylenes occur in small concentrations in crude oil, xylenes are produced mainly as part of the BTX aromatics (benzene, toluene, and xylenes) extracted from the product of catalytic reforming known as "reformate." Xylenes are primarily used as solvents in various applications, such as in printing, rubber, and leather industries; and are a common component of ink, rubber, adhesives, thinning paints, varnishes, and cleaning agents (e.g., for steel, silicon wafers, integrated circuits). However, there is concern over the depletion of finite reserves of crude oil. Thus, there is an ongoing need to develop methods for producing aromatic hydrocarbons such as benzene and xylenes from feedstocks other than crude oil, for example from feedstocks derived from waste plastics.

BRIEF SUMMARY

Disclosed herein is a process for producing benzene and xylenes comprising (a) contacting a hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons, (b) optionally introducing at least a portion of the hydrocarbon product to a first aromatics separating unit to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons, (c) feeding at least a portion of the hydrocarbon product and/or at least a portion of the saturated hydrocarbons stream to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the saturated hydrocarbons stream, (d) introducing at least a portion of the reforming unit product to a second aromatics separating unit to produce a non-aromatics recycle stream and a second aromatics stream, wherein the second aromatics stream comprises $C_6+$ aromatic hydrocarbons, (e) recycling at least a portion of the non-aromatics recycle stream to the reforming unit, (f) introducing at least a portion of the first aromatics stream and/or the second aromatics stream to a third aromatics separating unit to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, and wherein the $C_8$ aromatics stream comprises xylenes and ethylbenzene, (g) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes, and (h) conveying at least a portion of the $C_{11}+$ aromatics stream to the hydroprocessing unit.

Also disclosed herein is a process for producing benzene and xylenes comprising (a) converting a plastic waste to a hydrocarbon liquid stream and a pyrolysis gas stream in a pyrolysis unit, (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons, (c) optionally introducing at least a portion of the hydrocarbon product to a first aromatics separating unit to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons, (d) feeding at least a portion of the hydrocarbon product and/or at least a portion of the saturated hydrocarbons stream to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the saturated hydrocarbons stream, (e) introducing at least a portion of the reforming unit product to a second aromatics separating unit to produce a non-aromatics recycle stream and a second aromatics stream, wherein the second aromatics stream comprises $C_6+$ aromatic hydrocarbons, (f) recycling at least a portion of the non-aromatics recycle stream to the reforming unit, (g) introducing at least a portion of the first aromatics stream and/or the second aromatics stream to a third aromatics separating unit to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, and wherein the $C_8$ aromatics stream comprises xylenes and ethylbenzene, (h) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes, and (i) conveying at least a portion of the $C_{11}+$ aromatics stream to the hydroprocessing unit.

Further disclosed herein is a system for producing benzene and xylenes comprising a pyrolysis unit, a hydroprocessing unit, an optional first aromatics separating unit, a reforming unit, a second aromatics separating unit, a third aromatics separating unit, and a disproportionation and transalkylation unit, wherein the pyrolysis unit is configured to receive a plastic waste and to produce a hydrocarbon liquid stream and a pyrolysis gas stream, wherein the hydroprocessing unit comprises a hydroprocessing catalyst, wherein the hydroprocessing unit is configured to receive hydrogen and at least a portion of the hydrocarbon liquid stream and to produce a hydrocarbon product and a first gas stream, wherein the hydrocarbon product comprises $C_5+$ hydrocarbons, wherein the hydrocarbon product comprises equal to or greater than about 90 wt. % $C_{10}-$ hydrocarbons, based on the total weight of the hydrocarbon product, and wherein the hydrocarbon product comprises less than about 1 wt. % olefins, based on the total weight of the hydrocarbon product, wherein the optional first aromatics separating unit is configured to receive at least a portion of the hydrocarbon product and to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons, wherein the reforming unit comprises a reforming catalyst, wherein the reforming unit is configured to receive at least a portion of the hydrocarbon product and/or at least a portion of the saturated hydrocarbons stream and to produce a reforming unit product, a second gas stream, and a hydrogen stream, wherein an amount of $C_6$ to $C_8$ aromatic hydrocarbons in the reforming unit product is greater than an amount of $C_6$ to $C_8$ aromatic hydrocarbons in the saturated hydrocarbons stream, wherein the second aromatics separating unit is configured to receive at least a portion of the reforming unit product and to produce a non-aromatics recycle stream and a second aromatics stream, and wherein the second aromatics stream comprises $C_6+$ aromatic hydrocarbons, wherein the third aromatics separating unit is configured to receive at least a portion of the first aromatics stream and/or the second aromatics stream and to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, wherein the $C_8$ aromatics stream comprises xylenes and ethylbenzene, and wherein at least a portion of the $C_{11}+$ aromatics stream is recycled to the hydroprocessing unit, and wherein the disproportionation and transalkylation unit comprises a disproportionation and transalkylation catalyst, wherein the disproportionation and transalkylation unit is configured to receive at least a portion of the $C_7$ aromatics stream, at least a portion of the $C_9$ aromatics stream, at least a portion of the $C_{10}$ aromatics stream, or combinations thereof and to produce a third aromatics stream, wherein the third aromatics stream comprises benzene and xylenes, and wherein a $C_9+$ aromatic hydrocarbons content of the combined first $C_6$ aromatics stream, $C_8$ aromatics stream, and third aromatics stream is less than about 5 wt. %, based on the weight of the combined first $C_6$ aromatics stream, $C_8$ aromatics stream, and third aromatics stream.

DETAILED DESCRIPTION

Figure 1:
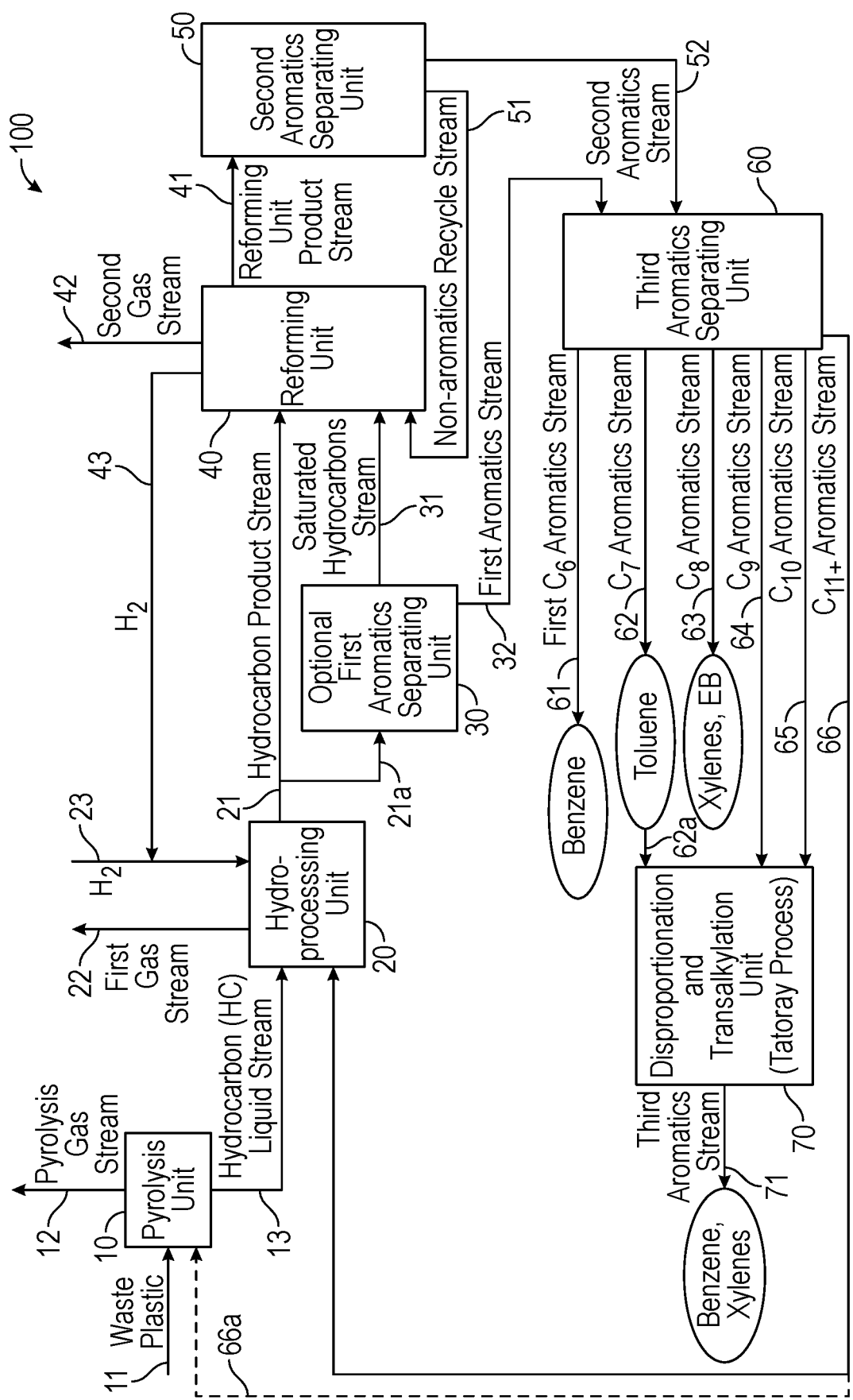
FIG. 1 displays a configuration of a system for producing benzene and xylenes.

Disclosed herein are processes and systems for producing high value products such as benzenes and xylenes from hydrocarbon liquid streams, for example hydrocarbon liquid streams produced by processing plastic waste. The process may include conversion of waste plastic while minimizing gases and maximizing liquid products, with high yields of aromatics like benzene, toluene, ethylbenzene and xylenes, along with small quantities of paraffins, iso-paraffins, olefins and naphthalenes. The plastic waste can be cracked or pyrolyzed by means of low temperature or high temperature pyrolysis, and by thermal or catalytic pyrolysis, wherein the composition of the pyrolysis product can be varied to maximize desired products by varying process conditions and catalysts. Benzene can then be recovered from a pyrolysis product, and remaining liquid products can be further converted to aromatics, such as benzene. To maximize benzene production, the liquid obtained from low severity and/or high severity pyrolysis can be further hydrocracked and/or hydrotreated to reduce a boiling point of the heavies (e.g., heavies can be cracked to mostly $C_{10-}$ hydrocarbons), and to also saturate liquid olefins. Hydrocracking and/or hydrotreating reactions to convert $C_{10+}$ heavies to $C_{10-}$ material can involve isomerization of naphthenes, dehydrocyclization of paraffins to naphthenes, dehydrogenation of naphthenes to aromatics, hydrocracking, and the like, or combinations thereof. A treated liquid recovered from hydrocracking and/or hydrotreating can be further sent to aromatics extraction and/or reforming to convert other hydrocarbons to aromatics. Aromatic products having more than 6 carbons can be converted to benzene through disproportionation. Heavies comprising $C_{9+}$ material along with toluene can be sent to disproportion and transalkylation reactions to maximize benzene and xylenes overall yields.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "X or more" means that the named component is present in an amount of the value X, and values which are more than X.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

For purposes of the disclosure herein, the term "amount" refers to a weight % of a given component in a particular composition, based upon the total weight of that particular composition (e.g., the total weight of all components present in that particular composition), unless otherwise indicated.

Processes for producing benzene and xylenes, for example from mixed plastics (e.g., plastic waste) are described in more detail with reference to FIG. 1.

Referring to FIG. 1, a benzene and xylenes production system 100 is disclosed. The benzene and xylenes production system 100 generally comprises a pyrolysis unit 10; a hydroprocessing unit 20; an optional first aromatics separating unit 30; a reforming unit 40; a second aromatics separating unit 50; a third aromatics separating unit 60; and a disproportionation and transalkylation unit (e.g., Tatoray unit) 70.

A process for producing benzene and xylenes can comprise a step of converting a plastic waste to a hydrocarbon liquid stream and a pyrolysis gas stream in a pyrolysis unit. The process can comprise introducing the waste plastics to a pyrolysis unit to produce a pyrolysis product, wherein the pyrolysis product comprises a gas phase and a liquid phase.

Mixed plastics (e.g., waste plastics) can be either placed in the pyrolysis unit 10 or fed to the pyrolysis unit 10 via waste plastic stream 11. In the pyrolysis unit 10, the waste plastic stream 11 is converted via pyrolysis to a pyrolysis product, wherein the pyrolysis product comprises a gas phase (e.g., pyrolysis gases, such as $C_1$ to $C_4$ gases, hydrogen ($H_2$), carbon monoxide (CO), carbon dioxide ($CO_2$), hydrochloric acid (HCl) gas, etc.) and a liquid phase (e.g., pyrolysis liquid).

Plastic waste which can be loaded into or fed to the pyrolysis unit 10 via waste plastic stream 11 may include post-consumer waste plastics, such as mixed plastic waste. Mixed plastics can comprise non-chlorinated plastics (e.g., polyolefins, polyethylene, polypropylene, polystyrene, copolymers, etc.), chlorinated plastics (e.g., polyvinylchloride (PVC), polyvinylidene chloride (PVDC), etc.), and the like, or mixtures thereof. Generally, waste plastics comprise long chain molecules or polymer hydrocarbons. Waste plastics as disclosed herein also include used tires.

The pyrolysis unit 10 may be any suitable vessel configured to convert waste plastics into gas phase and liquid phase products (e.g., simultaneously). The vessel may be configured for gas phase, liquid phase, vapor-liquid phase, gas-solid phase, liquid-solid phase, or slurry phase operation. The vessel may contain one or more beds of inert material or pyrolysis catalyst comprising sand, zeolite, alumina, a catalytic cracking catalyst, or combinations thereof. Generally, the pyrolysis catalyst is capable of transferring heat to the components subjected to the pyrolysis process in the pyrolysis unit 10. Alternatively, the pyrolysis unit 10 can be operated without any catalyst (e.g., pure thermal pyrolysis). The pyrolysis unit 10 may be operated adiabatically, isothermally, nonadiabatically, non-isothermally, or combinations thereof. The pyrolysis reactions of this disclosure may be carried out in a single stage or in multiple stages. For example, the pyrolysis unit 10 can be two reactor vessels fluidly connected in series.

In a configuration where the pyrolysis unit 10 comprises two vessels, the pyrolysis process may be divided into a first stage which is performed in a first vessel and in a second stage fluidly connected downstream of the first stage which is performed in the second vessel. As will be appreciated by one of skill in the art, and with the help of this disclosure, the second stage may enhance the pyrolysis of an intermediate pyrolysis product stream flowing from the first stage into the second stage, to yield a pyrolysis product flowing from the second stage. In some configurations, the first stage may utilize thermal cracking of the waste plastics, and the second stage may utilize thermal or catalytic cracking of the waste plastics to yield the pyrolysis product flowing from the second stage. Alternatively, the first stage may utilize catalytic cracking of the waste plastics, and the second stage may utilize thermal or catalytic cracking of the waste plastics to yield the pyrolysis product flowing from the second stage.

In some configurations, the pyrolysis unit 10 may include one or more equipment configured to convert mixed plastics into gas phase and liquid phase products. The one or more equipment may or may not contain an inert material or pyrolysis catalyst as described above. Examples of such equipment include one or more of heated extruders, heated rotating kiln, heated tank-type reactors, packed bed reactors, bubbling fluidized bed reactors, circulating fluidized bed reactors, empty heated vessels, enclosed heated surfaces where plastic flows down along the wall and cracks, vessels surrounded by ovens or furnaces, or any other suitable equipment offering a heated surface to assist in cracking.

The pyrolysis unit 10 can be configured to pyrolyse (e.g., crack), and in some aspects (e.g., where hydrogen is added to the pyrolysis unit 10), additionally hydrogenate components of the waste plastic stream 11 fed to the pyrolysis unit 10. Examples of reactions which may occur in the pyrolysis unit 10 include, but are not limited to isomerization of one or more normal paraffins to one or more i-paraffins, selective ring opening of one or more cycloparaffins to one or more i-paraffins, cracking of long chain length molecules to short chain length molecules, removal of heteroatoms from heteroatom-containing hydrocarbons (e.g., dechlorination), hydrogenation of coke generated in the process, or combinations thereof.

In one or more configurations of the pyrolysis unit 10, a head space purge gas can be utilized in all or a portion of the pyrolysis stage(s) (conversion of waste plastics to a liquid phase and/or gas phase products) to enhance cracking of plastics, produce valuable products, provide a feed for steam cracking, or combinations thereof. The head space purge gas may include hydrogen ($H_2$), $C_1$ to $C_4$ hydrocarbon gases (e.g., alkanes, methane, ethane, propane, butane, isobutane), inert gases (e.g., nitrogen ($N_2$), argon, helium, steam), and the like, or combinations thereof. The use of a head space purge gas assists in the dechlorination in the pyrolysis unit 10, when the waste plastic comprises chlorinated plastics. The head space purge gas may be introduced to the pyrolysis unit 10 to aid in the removal of volatiles entrained in the melted mixed plastics present in the pyrolysis unit 10.

A hydrogen ($H_2$) containing stream can be added to the pyrolysis unit 10 to enrich the pyrolysis unit environment with $H_2$, assist in stripping entrapped hydrogen in the pyrolysis unit, provide a local environment rich in hydrogen in the pyrolysis melt or liquid, or combinations thereof; for example via a $H_2$ containing stream fed directly to the pyrolysis unit independently of the waste plastic stream 11. In some aspects, $H_2$ can also be introduced along with stream 11 to the pyrolysis unit 10, with adequate safety measures incorporated for hydrogen handling with plastics feed.

The pyrolysis unit 10 may facilitate any reaction of the components of the waste plastic stream 11 in the presence of, or with, hydrogen. Reactions may occur such as the addition of hydrogen atoms to double bonds of unsaturated molecules (e.g., olefins), resulting in saturated molecules (e.g., paraffins, i-paraffins, naphthenes). Additionally or alternatively, reactions in the pyrolysis unit 10 may cause a rupture of a bond of an organic compound, with a subsequent reaction and/or replacement of a heteroatom with hydrogen.

The use of hydrogen in the pyrolysis unit 10 can have beneficial effects of i) reducing the coke as a result of cracking, ii) keeping the catalyst used (if any) in the process in an active condition, iii) improving removal of chloride from stream 11 such that the pyrolysis product from pyrolysis unit 10 is substantially dechlorinated with respect to waste plastic stream 11, which minimizes the chloride removal requirement in units downstream of the pyrolysis unit 10, iv) hydrogenating of olefins, v) reducing diolefins in pyrolysis product, vi) helping operate the pyrolysis unit 10 at reduced temperatures for same levels of conversion of waste plastic stream 11 in the pyrolysis unit 10, or combinations of i)-vi).

The pyrolysis processes in the pyrolysis unit 10 may be low severity or high severity. Low severity pyrolysis processes may occur at a temperature of 250° C. to 450° C., alternatively 275° C. to 425° C., or alternatively 300° C. to 400° C., and may produce pyrolysis oils rich in mono- and di-olefins as well as a significant amount of aromatics. High severity pyrolysis processes may occur at a temperature of 450° C. to 750° C., alternatively 500° C. to 700° C., or alternatively 550° C. to 650° C., and may produce pyrolysis oils rich in aromatics.

An example of a pyrolysis process for waste plastics is disclosed in U.S. Pat. No. 8,895,790, which is incorporated by reference in its entirety. Another example of a pyrolysis process is disclosed in International Publication No. WO 2016/009333 A1, and U.S. patent application Ser. No. 15/085,445 filed Mar. 30, 2016, each of which is incorporated by reference in its entirety.

A pyrolysis product can be recovered as an effluent from the pyrolysis unit 10 and conveyed (e.g., flowed, for example via pumping, gravity, pressure differential, etc.) to a pyrolysis separating unit. The pyrolysis product can be separated in the pyrolysis separating unit into a pyrolysis gas stream 12 and a hydrocarbon liquid stream 13, wherein the pyrolysis gas stream 12 comprises at least a portion of the gas phase of the pyrolysis product, and wherein the hydrocarbon liquid stream 13 comprises at least a portion of the liquid phase of the pyrolysis product. The pyrolysis separating unit may comprise any suitable gas-liquid separator, such as a vapor-liquid separator, oil-gas separators, gas-liquid separators, degassers, deliqulizers, scrubbers, traps, flash drums, compressor suction drums, gravity separators, centrifugal separators, filter vane separators, mist eliminator pads, liquid-gas coalescers, distillation columns, and the like, or combinations thereof.

In some configurations, the pyrolysis separating unit can be a condenser which operates at conditions which condense a portion of the pyrolysis product into hydrocarbon liquids (e.g., liquid product) while leaving the hydrocarbon gases in the gas phase (e.g., gas product). A liquid product flows from the pyrolysis separating unit in hydrocarbon liquid stream 13, and a gas product flows from the pyrolysis separating unit in pyrolysis gas stream 12. The pyrolysis gas stream 12 can comprise $H_2$, $C_1$ to $C_4$ hydrocarbons, inert gases (e.g., nitrogen ($N_2$), argon, helium, steam, CO, $CO_2$), and the like, or combinations thereof.

The hydrocarbon liquid stream 13 can comprise paraffins, i-paraffins, olefins, naphthenes, aromatic compounds, organic chlorides, or combinations thereof. When the hydrocarbon liquid stream 13 comprises paraffins, i-paraffins, olefins, naphthenes, and aromatic compounds, the stream can be referred to as a PIONA stream; and when the hydrocarbon liquid stream 13 comprises paraffins, olefins, naphthenes, and aromatic compounds, the stream can be referred to as a PONA stream. In some aspects, the hydrocarbon liquid stream 13 can comprise a plastic pyrolysis oil and/or a tire pyrolysis oil.

As discussed herein, aspects of the processes disclosed herein contemplate hydrocracking of molecules, and in particular, heavy hydrocarbon molecules of the hydrocarbon liquid stream 13. As such, it is contemplated that at least a portion of the hydrocarbon liquid stream 13 comprises heavy hydrocarbon molecules (e.g., also referred to as heavy ends of pyrolysis oils). In an aspect, an amount of heavy hydrocarbon molecules in the hydrocarbon liquid stream 13 may be less than 10 wt. %, based on the total weight of the hydrocarbon liquid stream 13. Alternatively, the amount of the heavy hydrocarbon molecules in the hydrocarbon liquid stream 13 may be from 10 wt. % to 90 wt. %, based on the total weight of the hydrocarbon liquid stream 13. As will be described in more detail later herein, the heavy hydrocarbon molecules may include paraffins, i-paraffins, olefins, naphthenes, aromatic hydrocarbons, or combinations thereof. In some aspects, the heavy hydrocarbon molecules may include $C_{16}$ and larger hydrocarbons. Greater than 5, 10, 15, 20, 25, 30 wt. % or more of the heavy hydrocarbon molecules in the hydrocarbon liquid stream 13 is hydrocracked in the hydroprocessing unit 20.

Examples of paraffins which may be present in the hydrocarbon liquid stream 13 include, but are not limited to, $C_1$ to $C_{22}$ n-paraffins and i-paraffins. The paraffins can be present in the hydrocarbon liquid stream 13 in an amount of less than 10 wt. % based on the total weight of the hydrocarbon liquid stream 13. Alternatively, the paraffins can be present in the hydrocarbon liquid stream 13 in an amount of 10 wt. %, 20 wt. %, 30 wt. %, 40 wt. %, 50 wt. %, 60 wt. %, or more based on the total weight of the hydrocarbon liquid stream 13. While certain hydrocarbon liquid streams include paraffins of carbon numbers up to 22, the present disclosure is not limited to carbon number 22 as an upper end-point of the suitable range of paraffins, and the paraffins can include higher carbon numbers, e.g., 23, 24, 25, 26, 27, 28, 29, 30, 31, 32, 33, 34, 35, 36, 37, 38, 39, 40, and higher. In some aspects, at least a portion of the paraffins in the hydrocarbon liquid stream 13 comprises at least a portion of the heavy hydrocarbon molecules.

Examples of olefins which may be present in hydrocarbon liquid stream 13 include, but are not limited to, $C_2$ to $C_{10}$ olefins and combinations thereof. Where hydrogen is introduced to the pyrolysis unit 10, due to hydrogenation reactions in the pyrolysis unit 10, the olefins can be present in the hydrocarbon liquid stream 13 in an amount of less than 10 wt. %, based on the total weight of the hydrocarbon liquid stream 13. Alternatively, the olefins can be present in the hydrocarbon liquid stream 13 in an amount of 5 wt. %, 10 wt. %, 20 wt. %, 30 wt. %, 40 wt. %, or more based on the total weight of the hydrocarbon liquid stream 13. While certain hydrocarbon streams include olefins of carbon numbers up to 10, the present disclosure is not limited to carbon number 10 as an upper end-point of the suitable range of olefins, and the olefins can include higher carbon numbers, e.g., 11, 12, 13, 14, 15, 16, 17, 18, 19, 20, 21, 22, 23, 24, 25, 26, 27, 28, 29, 30, and higher. In some aspects, at least a portion of the one or more olefins in the hydrocarbon liquid stream 13 comprise at least a portion of the heavy hydrocarbon molecules. Alternatively, none of the heavy hydrocarbon molecules in the hydrocarbon liquid stream 13 are olefins.

In some aspects, the hydrocarbon liquid stream 13 comprises no olefins, e.g., the hydrocarbon liquid stream 13 is substantially free of olefins. In some aspects, the hydrocarbon liquid stream 13 comprises less than 1, 0.1, 0.01, or 0.001 wt. % olefins.

Examples of naphthenes which may be present in the hydrocarbon liquid stream 13 include, but are not limited to, cyclopentane, cyclohexane, cycloheptane, and cyclooctane. The naphthenes can be present in the hydrocarbon liquid stream 13 in an amount of less than 10 wt. %, based on the total weight of the hydrocarbon liquid stream 13. Alternatively, the naphthenes can be present in the hydrocarbon liquid stream 13 in an amount of 10 wt. %, 20 wt. %, 30 wt. %, 40 wt. %, or more based on the total weight of the hydrocarbon liquid stream 13. While certain hydrocarbon streams include naphthenes of carbon numbers up to 8, the present disclosure is not limited to carbon number 8 as an upper end-point of the suitable range of naphthenes, and the naphthenes can include higher carbon numbers, e.g., 9, 10, 11, 12, 13, 14, 15, 16, 17, 18, 19, 20, 21, 22, 23, 24, 25, 26, 27, 28, 29, 30, and higher. In some aspects, at least a portion of the naphthenes in the hydrocarbon liquid stream 13 comprises at least a portion of the heavy hydrocarbon molecules.

The hydrocarbon liquid stream 13 may comprise aromatic hydrocarbons with carbon numbers of 6, 7, 8, 9, 10, 11, 12, 13, 14, 15, 16, 17, 18, 19, 20, 21, 22, 23, 24, 25, 26, 27, 28, 29, 30, and higher. In an aspect, the aromatic hydrocarbons carbon number can be as high as 22. Nonlimiting examples of aromatic hydrocarbons suitable for use in the present disclosure as part of the hydrocarbon liquid stream include benzene, toluene, xylenes, ethylbenzene, propylbenzenes, trimethylbenzenes, tetramethylbenzenes, butylbenzenes, dimethylnaphthalene, biphenyl, and the like, or combinations thereof. The aromatic hydrocarbons can be present in the hydrocarbon liquid stream 13 in an amount of 5 wt. %, 10 wt. %, 15 wt. %, 20 wt. %, 25 wt. %, 30 wt. %, 35 wt. %, 40 wt. %, 50 wt. %, 60 wt. %, or more based on the total weight of the hydrocarbon liquid stream 13. In some aspects, at least a portion of the aromatic hydrocarbons in the hydrocarbon liquid stream 13 comprises at least a portion of the heavy hydrocarbon molecules.

A process for producing benzene and xylenes can comprise a step of contacting the hydrocarbon liquid stream 13 with a hydroprocessing catalyst in the presence of hydrogen (e.g., hydrogen stream 23) in the hydroprocessing unit 20 to yield a hydrocarbon product stream 21 and a first gas stream 22, wherein the hydrocarbon product stream 21 comprises $C_5+$ hydrocarbons. The first gas stream 22 can comprise $H_2$, $C_1$ to $C_4$ hydrocarbons, inert gases (e.g., nitrogen ($N_2$), argon, helium, steam, CO, $CO_2$), and the like, or combinations thereof.

The hydroprocessing unit 20 can be any suitable hydroprocessing reactor (e.g., hydroprocessor), such as a hydrocracker, a catalytic cracker operated in hydropyrolysis mode, a fluid catalytic cracker operated in hydropyrolysis mode, a hydrotreater, and the like, or combinations thereof. The hydroprocessing unit 20 is configured to hydrocrack long chain molecules (e.g., heavy hydrocarbon molecules contained in the hydrocarbon liquid stream 13), hydrogenate and dechlorinate (where stream 13 contains chloride) components of the hydrocarbon liquid stream 13 fed to the hydroprocessing unit 20. In the hydroprocessing unit 20, the hydrocarbon liquid stream 13 is contacted with a hydroprocessing catalyst in the presence of hydrogen to yield the hydrocarbon product stream 21. It is contemplated that the hydrocarbon liquid stream 13 may be contacted with the hydroprocessing catalyst in upward flow, downward flow, radial flow, or combinations thereof, with or without a staged addition of hydrocarbon liquid stream 13, a $H_2$ stream, or combinations thereof.

The hydroprocessing unit 20 may be any vessel configured to contain the hydroprocessing catalyst disclosed herein. The vessel may be configured for gas phase, liquid phase, vapor-liquid phase, gas-liquid-solid phase, or slurry phase operation. The hydroprocessing unit 20 may include one or more beds of the hydroprocessing catalyst in fixed bed, fluidized bed, moving bed, ebullated bed, slurry bed, or combinations thereof, configuration. The hydroprocessing unit 20 may be operated adiabatically, isothermally, nonadiabatically, non-isothermally, or combinations thereof. In an aspect, the hydroprocessing unit 20 may comprise one or more vessels.

The hydroprocessing unit 20 may facilitate any reaction of the components of the hydrocarbon liquid stream 13 in the presence of, or with, hydrogen. Reactions may occur as the addition of hydrogen atoms to double bonds of unsaturated molecules (e.g., olefins, aromatic compounds), resulting in saturated molecules (e.g., paraffins, i-paraffins, naphthenes). Additionally, reactions in the hydroprocessing unit 20 may cause a rupture of a bond of an organic compound, resulting in "cracking" of a hydrocarbon molecule into two or more smaller hydrocarbon molecules, or resulting in a subsequent reaction and/or replacement of a heteroatom with hydrogen. Examples of reactions which may occur in the hydroprocessing unit 20 include, but are not limited to, the hydrogenation of olefins, removal of heteroatoms from heteroatom-containing hydrocarbons (e.g., dechlorination), hydrocracking of large paraffins or i-paraffins to smaller hydrocarbon molecules, hydrocracking of aromatic hydrocarbons to smaller cyclic or acyclic hydrocarbons, conversion of one or more aromatic compounds to one or more cycloparaffins, isomerization of one or more normal paraffins to one or more i-paraffins, selective ring opening of one or more cycloparaffins to one or more i-paraffins, or combinations thereof.

In an aspect, contacting the hydrocarbon liquid stream 13 with the hydroprocessing catalyst in the presence of hydrogen yields $C_1$ to $C_4$ gases and $C_5+$ ($C_5$ and heavier) liquid hydrocarbons. When the waste plastic stream 11 contains chloride, it is contemplated that dechlorination using the hydroprocessing catalyst as described herein can be performed in the hydroprocessing unit 20 without the use of chlorine sorbents, without addition of $Na_2CO_3$ in an effective amount to function as a dechlorinating agent, or both.

The hydroprocessing catalyst may be any catalyst used for hydrogenation (e.g., saturation) of olefins and aromatic hydrocarbons (e.g., a commercially available hydrotreating catalyst). The hydroprocessing catalyst can comprise a cobalt and molybdenum catalyst (Co—Mo catalyst) on an alumina support, a nickel and molybdenum catalyst (Ni—Mo catalyst) on an alumina support, a tungsten and molybdenum catalyst (W—Mo catalyst) on an alumina support, cobalt and molybdenum oxides on an alumina support, nickel and molybdenum oxides on an alumina support, tungsten and molybdenum oxides on an alumina support, cobalt and molybdenum sulphides on an alumina support, nickel and molybdenum sulphides on an alumina support, tungsten and molybdenum sulphides on an alumina support, a zeolite comprising one or more metals, and the like, or combinations thereof. Other catalysts suitable for use as the hydroprocessing catalyst may include platinum and palladium catalyst (Pt—Pd catalyst) on an alumina support, nickel sulphides suitable for slurry processing, molybdenum sulphides suitable for slurry processing, and the like, or combinations thereof. The zeolites can comprise ZSM-5, ZSM-11, Y, high-silica Y, USY, and the like, or combinations thereof. Each metal of the one or more metals of the zeolite can be independently selected from the group consisting of cobalt, molybdenum, tungsten, nickel, titanium, copper, magnesium, tin, iron, zinc, tungsten, vanadium, gallium, calcium, manganese, ruthenium and rhenium.

In configurations where the hydrocarbon liquid stream 13 comprises one or more sulphides and one or more chloride compounds, contacting the hydrocarbon liquid stream 13 with the hydroprocessing catalyst acts to activate the hydroprocessing catalyst by sulphiding and to acidify the hydroprocessing catalyst by chlorinating. Continuously contacting the hydroprocessing catalyst with the hydrocarbon liquid stream 13 containing one or more sulphides, one or more chloride compounds, or both, may maintain catalyst activity on a continuous basis. For purposes of the disclosure herein, the term "catalyst activity" or "catalytic activity" with respect to the hydroprocessing catalyst refers to the ability of the hydroprocessing catalyst to catalyze hydroprocessing reactions, such as hydrocracking reactions, hydrodechlorination reactions, etc.

A hydrogen stream 23 can be added to the hydroprocessing unit 20 to enrich the hydroprocessing unit environment with $H_2$, for example via stream 23 fed directly to the hydroprocessing unit independently of the hydrocarbon liquid stream 13. Additionally or alternatively, a $H_2$ containing stream can be added to the hydrocarbon liquid stream 13 before entering the hydroprocessing unit 20. The rate of hydrogen addition to the hydroprocessing unit 20 is generally sufficient to achieve the hydrogen to hydrocarbon ratios disclosed herein.

The disclosed hydroprocessing unit 20 may operate at various process conditions. For example, contacting the hydrocarbon liquid stream 13 with the hydroprocessing catalyst in the presence of hydrogen may occur in the hydroprocessing unit 20 at a temperature of from 250° C. to 600° C.; alternatively, 275° C. to 550° C.; or alternatively, 300° C. to 500° C. The temperature in the hydroprocessing unit 20 can be attained by using a feed (e.g., hydrocarbon liquid stream 13) pre-heating furnace and/or feed-hydroprocessing unit effluent heat exchangers. Contacting the hydrocarbon liquid stream 13 with the hydroprocessing catalyst in the presence of hydrogen may occur in the hydroprocessing unit 20 at a pressure of 1 barg to 200 barg, alternatively, 10 barg to 150 barg, or alternatively, 20 barg to 60 barg. Contacting the hydrocarbon liquid stream 13 with the hydroprocessing catalyst in the presence of hydrogen may occur in the hydroprocessing unit 20 at a weight hourly space velocity (WHSV) of between 0.1 $hr^{-1}$ to 10 $hr^{-1}$; or alternatively, 1 $hr^{-1}$ to 3 $hr^{-1}$. Contacting the hydrocarbon liquid stream 13 with the hydroprocessing catalyst in the presence of hydrogen may occur in the hydroprocessing unit 20 at a hydrogen to hydrocarbon ($H_2$/HC) flow ratio of from 10 NL/L to 3,000 NL/L; or alternatively, from 200 NL/L to 800 NL/L.

In some configurations, the hydroprocessing unit 20 can be a mild hydrocracking unit, such as a mild hydrocracker used in refining operations, wherein the hydroprocessing unit 20 can operate at pressures of up to 100 barg and at temperatures of up to 430° C. As will be appreciated by one of skill in the art, and with the help of this disclosure, the hydroprocessing unit 20 could operate at lower pressures to economize on hydrogen consumption and to preserve monoring aromatics (and only saturate di- and poly-aromatics, and olefins). Generally, mild hydrocracking units can saturate liquid olefins introduced to the mild hydrocracking unit, as well as reduce the heavies by selective cracking and hydrogenation, such that at least a portion of the mono-ring aromatics can be preserved. As will be appreciated by one of skill in the art, and with the help of this disclosure, since plastic pyrolysis oils are rich in hydrogen content compared to petroleum residues, it is possible to carry out the hydroprocessing at lower pressures of less than 100 barg. Further, as will be appreciated by one of skill in the art, and with the help of this disclosure, higher pressures of more than 100 barg can also be used with plastic pyrolysis oils.

In some aspects, the hydroprocessing unit 20 can further comprise a hydrodealkylating unit, wherein the hydrodealkylating unit can comprise a hydrodealkylating catalyst. The hydrodealkylating unit can be any suitable hydroprocessing reactor, such as a hydrocracker, a catalytic cracker operated in hydropyrolysis mode, a fluid catalytic cracker operated in hydropyrolysis mode, a hydrotreater, a hydrodealkylating reactor, and the like, or combinations thereof. The hydrodealkylating unit can be configured to hydrodealkylate, and in some configurations, additionally hydrocrack, dechlorinate and hydrogenate components of the hydrocarbon liquid stream 13.

The hydrodealkylating unit may be any vessel configured to contain the hydrodealkylating catalyst disclosed herein. The vessel may be configured for gas phase, liquid phase, vapor-liquid phase, gas-solid phase, gas-liquid-solid phase, or slurry phase operation. The hydrodealkylating unit may include one or more beds of the hydrodealkylating catalyst in fixed bed, fluidized bed, moving bed, ebullated bed, slurry bed, or combinations thereof, configuration. The hydrodealkylating unit may be operated adiabatically, isothermally, nonadiabatically, non-isothermally, or combinations thereof. In an aspect, the hydrodealkylating unit may comprise one or more vessels.

The hydrodealkylating unit may facilitate any suitable reaction of the components of the hydrocarbon liquid stream 13 in the presence of, or with, hydrogen. Reactions in the hydrodealkylating unit include a hydrodealkylation reaction of $C_9$+ aromatic hydrocarbons, wherein the $C_9$+ aromatic hydrocarbons in the presence of hydrogen form lower molecular weight aromatic hydrocarbons (e.g., $C_{6-8}$ aromatic hydrocarbons) and alkanes. For example, trimethylbenzenes can undergo a hydrodealkylation reaction to produce xylenes and methane. Other reactions may occur in the hydrodealkylating unit, such as the addition of hydrogen atoms to double bonds of unsaturated molecules (e.g., olefins, aromatic compounds), resulting in saturated molecules (e.g., paraffins, i-paraffins, naphthenes). Additionally, reactions in the hydrodealkylating unit may cause a rupture of a bond of an organic compound, resulting in "cracking" of a hydrocarbon molecule into two or more smaller hydrocarbon molecules, or resulting in a subsequent reaction and/or replacement of a heteroatom with hydrogen. Examples of reactions which may occur in the hydrodealkylating unit include, but are not limited to, hydrodealkylation of $C_9$+ aromatic hydrocarbons, the hydrogenation of olefins, removal of heteroatoms from heteroatom-containing hydrocarbons (e.g., dechlorination), hydrocracking of large paraffins or i-paraffins to smaller hydrocarbon molecules, hydrocracking of aromatic hydrocarbons to smaller cyclic or acyclic hydrocarbons, conversion of one or more aromatic compounds to one or more cycloparaffins, isomerization of one or more normal paraffins to one or more i-paraffins, selective ring opening of one or more cycloparaffins to one or more i-paraffins, or combinations thereof.

The hydrodealkylating catalyst may be any suitable catalyst used for hydrogenation (e.g., saturation) of olefins and aromatic hydrocarbons (e.g., a commercially available hydrotreating catalyst), such as the catalyst described for the hydroprocessing catalyst. Additionally, the hydrodealkylating catalyst may be any suitable hydrodealkylation catalyst (e.g., a commercially available hydrodealkylation catalyst), such as chromium oxides on an alumina support, chromium oxides on a silica support, molybdenum oxides on an alumina support, molybdenum oxides on a silica support, platinum on an alumina support, platinum on a silica support, platinum oxides on an alumina support, platinum oxides on a silica support, and the like, or combinations thereof.

The hydrocarbon product stream 21 comprises $C_5$+ liquid hydrocarbons, wherein the $C_5$+ liquid hydrocarbons comprise heavy hydrocarbon molecules. An amount of heavy hydrocarbon molecules in the hydrocarbon product stream 21 is less than an amount of heavy hydrocarbon molecules in the hydrocarbon liquid stream 13 due to hydrocracking of at least a portion of heavy hydrocarbon molecules from the hydrocarbon liquid stream during the step of contacting the hydrocarbon liquid stream 13 with a hydroprocessing catalyst in the presence of hydrogen in the hydroprocessing unit 20.

In some aspects, the hydrocarbon product stream 21 can comprise equal to or greater than about 90 wt. %, alternatively equal to or greater than about 92.5 wt. %, or alternatively equal to or greater than about 95 wt. % $C_{10}$− hydrocarbons, based on the total weight of the hydrocarbon product stream 21. As will be appreciated by one of skill in the art, and with the help of this disclosure, the conditions inside the hydroprocessing unit 20 can be such that the produced hydrocarbon product comprises mostly $C_{10}$− hydrocarbons.

In some aspects, the hydrocarbon product stream 21 can comprise less than about 1 wt. % olefins, based on the total weight of the hydrocarbon product stream 21.

A process for producing benzene and xylenes can comprise a step of optionally introducing at least a portion 21a of the hydrocarbon product stream to the first aromatics separating unit 30 to produce a saturated hydrocarbons stream 31 and a first aromatics stream 32, wherein the saturated hydrocarbons stream 31 comprises $C_5$+ saturated hydrocarbons, and wherein the first aromatics stream 32 comprises $C_6$+ aromatic hydrocarbons. As will be appreciated by one of skill in the art, and with the help of this disclosure, the $C_{5+}$ saturated hydrocarbons of the saturated hydrocarbons stream 31 (i) exclude $C_{6+}$ aromatic hydrocarbons; (ii) exclude $C_{5+}$ olefins; and (iii) include $C_{5+}$ paraffins, iso-paraffins and naphthenes. The first aromatics stream 32 comprises $C_6$ aromatic hydrocarbons, $C_7$ aromatic hydrocarbons, $C_8$ aromatic hydrocarbons, $C_9$ aromatic hydrocarbons, $C_{10}$ aromatic hydrocarbons, and combinations thereof.

The first aromatics separating unit 30 can comprise any suitable separating unit that is configured to separate the hydrocarbon product stream 21 into the saturated hydrocarbons stream 31 and the first aromatics stream 32. For example, the first aromatics separating unit 30 can employ selective adsorption, selective absorption, extractive distillation, solvent extraction followed by distillation, and the like, or combinations thereof.

A process for producing benzene and xylenes can comprise a step of feeding at least a portion of the hydrocarbon product stream 21 and/or at least a portion of the saturated hydrocarbons stream 31 to the reforming unit 40 (e.g., reformer 40) to produce a reforming unit product stream 41 (e.g., reformer product stream 41), a second gas stream 42, and a hydrogen stream 43, wherein the reforming unit 40 comprises a reforming catalyst. In an aspect, at least a portion of the hydrogen stream 43 can be recycled to the hydroprocessing unit 20, for example via hydrogen stream 23. The second gas stream 42 can comprise $H_2$ and $C_1$ to $C_4$ hydrocarbons.

In some aspects, at least a portion of the pyrolysis gas stream 12, at least a portion of the first gas stream 22, at least a portion of the second gas stream 42, or combinations thereof can be used as a fuel in the pyrolysis unit 10, the hydroprocessing unit 20, the reforming unit 40, or combinations thereof.

The reforming unit 40 can comprise any suitable aromatizing unit, such as a continuous catalytic reformer (CCR), a semi-regenerative reformer, an AROMAX unit, and the like, or combinations thereof. Aromatizing units generally produce aromatics from naphthenes and paraffins, as a source of specific aromatic compounds. In some aspects, the feed to the reforming unit 40 (e.g., hydrocarbon product stream 21 and/or saturated hydrocarbons stream 31) can be generally restricted to $C_6$ through $C_{10}$ compounds to maximize the production of $C_6$ to $C_8$ aromatic hydrocarbons, such as benzene, toluene, and xylenes. In an aspect, an amount of $C_6$ to $C_8$ aromatic hydrocarbons in the reforming unit product stream 41 is greater than an amount of $C_6$ to $C_8$ aromatic hydrocarbons in the hydrocarbon product stream 21 and/or saturated hydrocarbons stream 31.

The reforming unit 40 may facilitate any suitable reaction of the components of the hydrocarbon product stream 21 and/or saturated hydrocarbons stream 31 in the presence of the reforming catalyst. Reactions in the reforming unit 40 include dehydrogenation of naphthenes to aromatics; isomerisation of paraffins and naphthenes; dehydrocyclization of paraffins to aromatics; and the like; or combinations thereof.

The reforming catalyst may be any suitable catalyst used for hydrocarbon aromatization. The reforming catalyst can be monometallic (e.g., Pt), bimetallic (Pt, Re), multimetallic (e.g., Pt, Re, Pd, Ni, etc.). The metals of the reforming catalyst generally promote dehydrogenation and hydrogenation, as well as contribute to dehydrocyclization and isomerization. The reforming catalyst can have acid activity (e.g., halogens/silica incorporated in alumina base). The acid activity promotes isomerization, the initial step in hydrocracking, as well as participation in paraffin dehydrocyclization.

The reforming unit product stream 41 can comprise equal to or greater than about 55 wt. %, 65 wt. %, or 75 wt. % aromatic hydrocarbons, and less than about 45 wt. %, 35 wt. %, or 25 wt. % non-aromatic hydrocarbons (e.g., paraffins, iso-paraffins, naphthenes); based on the total weight of the reforming unit product stream 41.

A process for producing benzene and xylenes can comprise a step of introducing at least a portion of the reforming unit product stream 41 to the second aromatics separating unit 50 to produce a non-aromatics recycle stream 51 and a second aromatics stream 52, wherein the second aromatics stream 52 comprises $C_6$+ aromatic hydrocarbons. The second aromatics stream 52 comprises $C_6$ aromatic hydrocarbons, $C_7$ aromatic hydrocarbons, $C_8$ aromatic hydrocarbons, $C_9$ aromatic hydrocarbons, $C_{10}$ aromatic hydrocarbons, and combinations thereof. As will be appreciated by one of skill in the art, and with the help of this disclosure, the non-aromatics recycle stream 51 (i) excludes $C_{6+}$ aromatic hydrocarbons; and (ii) includes $C_{5+}$ paraffins, iso-paraffins and naphthenes. Further, as will be appreciated by one of skill in the art, and with the help of this disclosure, a feed to a reforming unit or reformer generally contains paraffins, iso-paraffins, naphthenes, and aromatics, and no olefins; however, the aromatics can be separated from a feed to the reforming unit, and in such case the feed to the reforming unit may contain paraffins, iso-paraffins and naphthenes, as is the case for non-aromatics recycle stream 51 and/or saturated hydrocarbons stream 31.

The second aromatics separating unit 50 can comprise any suitable separating unit that is configured to separate the reforming unit product stream 41 into the non-aromatics recycle stream 51 and the second aromatics stream 52. For example, the second aromatics separating unit 50 can employ selective adsorption, selective absorption, extractive distillation, solvent extraction followed by distillation, and the like, or combinations thereof.

In some aspects, at least a portion of the non-aromatics recycle stream 51 can be recycled to the reforming unit 40. In other aspects, at least a portion of the non-aromatics recycle stream 51 can be recycled to the pyrolysis unit 10 and/or the hydroprocessing unit 20. As will be appreciated by one of skill in the art, and with the help of this disclosure, when the desired products are liquid aromatics, it is preferable to recycle the non-aromatics recycle stream 51 to the reforming unit 40. Further, as will be appreciated by one of skill in the art, and with the help of this disclosure, when it is desired to maximize gas products, such as pyrolysis gas stream 12 and/or first gas stream 22, it is preferable to recycle the non-aromatics recycle stream 51 to the pyrolysis unit 10 and/or the hydroprocessing unit 20, respectively.

A process for producing benzene and xylenes can comprise a step of introducing at least a portion of the first aromatics stream 32 and/or at least a portion of the second aromatics stream 52 to the third aromatics separating unit 60 to produce a first $C_6$ aromatics stream 61, a $C_7$ aromatics stream 62, a $C_8$ aromatics stream 63, a $C_9$ aromatics stream 64, a $C_{10}$ aromatics stream 65, and a $C_{11}+$ aromatics stream 66, wherein the first $C_6$ aromatics stream 61 comprises benzene, wherein the $C_7$ aromatics stream 62 comprises toluene, and wherein the $C_8$ aromatics stream 63 comprises xylenes and ethylbenzene (EB). The $C_9$ aromatics stream 64 can comprise trimethylbenzene, methylethylbenzene, propylbenzene, and the like, or combinations thereof. The $C_{10}$ aromatics stream 65 can comprise tetramethylbenzene, diethylbenzene, dimethylethylebenzene, methylpropylbenzene, and the like, or combinations thereof.

The third aromatics separating unit 60 can comprise any suitable separating unit that is configured to separate the first aromatics stream 32 and/or the second aromatics stream 52 into its components (e.g., streams 61, 62, 63, 64, 65, and 66). In some aspects, the third aromatics separating unit 60 can comprise one or more distillation columns. Generally, the one or more distillation columns can separate components of the first aromatics stream 32 and/or the second aromatics stream 52 based on their boiling points.

In some aspects, at least a portion of the $C_{11}+$ aromatics stream 66 can be conveyed to the hydroprocessing unit 20. In other aspects, a portion 66a of the $C_{11}+$ aromatics stream can be conveyed to the pyrolysis unit 10. The $C_{11}+$ aromatics stream 66 can comprise methylbutylbenzene, diethylmethylbenzene, pentamethylbenzene, 1-methylnaphthalene, 2-methylnaphthalene, 2-ethylnaphthalaene, dimethylnaphthalaene, and the like, or combinations thereof.

In some aspects, the process for producing benzene and xylenes can further comprise separating the $C_8$ aromatics stream 63 into a first xylenes stream and an EB stream, for example via extractive distillation, fractional crystallization, selective adsorption using molecular sieves, or combinations thereof. The first xylenes stream can comprise p-xylene. The EB stream can comprise EB, and o-xylene and m-xylene.

In some aspects, at least a portion of the EB stream can be further isomerized to produce xylenes (e.g., p-xylene) in an isomerizing unit, wherein the isomerizing unit comprises an isomerization catalyst. The isomerization catalyst can comprise an acid catalyst, for example a bifunctional catalyst. As will be appreciated by one of skill in the art, and with the help of this disclosure, bifunctional isomerization catalysts are more stable to deactivation by coking than monofunctional isomerization catalysts. Bifunctional isomerization catalysts can comprise a zeolite (e.g., ZSM-5, mordenite) and a noble metal (e.g., Pt) supported on alumina or silica-alumina. Hydrogen can be introduced to the isomerizing unit to avoid catalyst coking.

In other aspects, at least a portion of the EB stream can be further dealkylated to produce benzene in a dealkylation unit, wherein the dealkylation unit comprises a dealkylation catalyst. The main product of EB dealkylation is benzene, and the dealkylation catalyst generally comprises a metal loaded zeolite, wherein the metal can be Pt, Pd, Ni, Mo, etc.

A process for producing benzene and xylenes can comprise a step of contacting at least a portion 62a of the $C_7$ aromatics stream, at least a portion of the $C_9$ aromatics stream 64, at least a portion of the $C_{10}$ aromatics stream 65, at least a portion of the EB stream, or combinations thereof with a disproportionation and transalkylation catalyst in the presence of hydrogen in a disproportionation and transalkylation unit 70 to yield a third aromatics stream 71, wherein the third aromatics stream 71 comprises benzene and xylenes. In an aspect, the disproportionation and transalkylation unit 70 comprises a Tatoray unit, i.e., a disproportionation and transalkylation unit housing a Tatoray process (e.g., disproportionation and transalkylation process).

A disproportionation and transalkylation process (e.g., Tatoray process) is generally used to selectively convert toluene and $C_9$ aromatics, and in some cases $C_{10}$ aromatics, into benzene and xylenes, for example to maximize xylenes (e.g., para-xylene) production. The Tatoray process produces mixed xylenes from toluene and heavy aromatics. As will be appreciated by one of skill in the art, and with the help of this disclosure, a Tatoray process generally shifts chemical equilibrium from benzene production to xylenes production.

The two major reactions in a Tatoray process are disproportionation and transalkylation. For purposes of the disclosure herein, the conversion of toluene into benzene and xylenes can be referred to as "disproportionation" (e.g., toluene disproportionation). Further, for purposes of the disclosure herein, the term "transalkylation" refers to the conversion of a mixture of toluene and $C_9$ aromatics, and in some cases $C_{10}$ aromatics into xylenes. Tatoray process reactions are conducted in a hydrogen atmosphere to minimize coke formation on catalyst. Because there is negligible ring destruction in the Tatoray process, there is very little hydrogen consumption. Most of the hydrogen consumption in a Tatoray process can be attributed to the cracking of the non-aromatic impurities in the feed to the Tatoray unit (e.g., disproportionation and transalkylation unit 70). Generally, the Tatoray process can be conducted at a total pressure of about 10-50 atm, at a temperature of about 350-530° C., at a hydrogen to hydrocarbon ratio of about 0.5-20 mole/mole; and at a hydrogen concentration in recycled gas to Tatoray unit (e.g., disproportionation and transalkylation unit 70) of about 70 mol % or higher. A feed to the Tatoray unit along with fresh and/or recycle hydrogen can be preheated in a furnace, and then fed to the Tatoray unit. The Tatoray process can be carried out in an adiabatic fixed bed reactor (e.g., Tatoray unit). Undesired aromatics (e.g., toluene, $C_{9+}$ aromatics) in a product from the Tatoray unit can be recovered from such product and recycled back to a feed to the Tatoray unit.

In an aspect, the process for producing benzene and xylenes can further comprise conveying at least a portion of the hydrogen stream 43 to the disproportionation and transalkylation unit 70.

Nonlimiting examples of disproportionation and transalkylation catalysts suitable for use in the present disclosure include a zeolite; a ZSM-5 characterized by Si/Al ratio of equal to or greater than about 15:1; a metal loaded ZSM-5, wherein the metal comprises platinum, molybdenum, magnesium, rhenium, or combinations thereof; mordenite; a bismuth oxide loaded mordenite; beta zeolite; MCM-22; and the like; or combinations thereof.

In an aspect, a $C_9+$ aromatic hydrocarbons content of the combined first $C_6$ aromatics stream 61, $C_8$ aromatics stream 63, and third aromatics stream 71 is less than about 5 wt. %, alternatively less than about 3 wt. %, or alternatively less than about 1 wt. %, based on the weight of the combined first $C_6$ aromatics stream 61, $C_8$ aromatics stream 63, and third aromatics stream 71.

In an aspect, the third aromatics stream 71 can be further separated into a second $C_6$ aromatics stream comprising benzene and a second xylenes stream, for example via distillation. In some aspects, the second xylenes stream comprises p-xylene, o-xylene and m-xylene. The second xylenes stream can be further separated into a p-xylene fraction, and an o-xylene and m-xylene fraction, for example via extractive distillation, fractional crystallization, selective adsorption using molecular sieves, or combinations thereof.

In an aspect, the process for producing benzene and xylenes as disclosed herein can be characterized by an overall benzene yield of equal to or greater than about 18 wt. %, alternatively equal to or greater than about 20 wt. %, or alternatively equal to or greater than about 23 wt. %. For purposes of the disclosure herein, all yields are calculated and reported as a weight % (wt. %) of the total weight of the plastic feed (e.g., plastic fed to a pyrolysis unit or pyrolyzer), unless otherwise specified. Further, for purposes of the disclosure herein, the overall benzene yield accounts for benzene recovered at any point from the process, for example via the first $C_6$ aromatics stream 61 and the second $C_6$ aromatics stream.

In an aspect, the process for producing benzene and xylenes as disclosed herein can be characterized by an overall xylenes yield of equal to or greater than about 20 wt. %, alternatively equal to or greater than about 25 wt. %, or alternatively equal to or greater than about 30 wt. %. For purposes of the disclosure herein, the overall xylenes yield accounts for xylenes recovered at any point from the process, for example via the first xylenes stream and the second xylenes stream.

In an aspect, the process for producing benzene and xylenes as disclosed herein can be characterized by an overall benzene and xylenes yield of equal to or greater than about 40 wt. %, alternatively equal to or greater than about 50 wt. %, or alternatively equal to or greater than about 55 wt. %.

A process for producing benzene and xylenes can comprise (a) converting a plastic waste to a hydrocarbon liquid stream and a pyrolysis gas stream in a low severity pyrolysis unit at a temperature of from about 350° C. to about 450° C. and/or in a high severity pyrolysis unit at a temperature of equal to or greater than about 450° C.; (b) contacting at least a portion of the hydrocarbon liquid stream with a hydroprocessing catalyst in the presence of hydrogen in a mild hydrocracker unit at a temperature of from about 300° C. to about 430° C. and at a pressure of from about 10 barg to about 100 barg to yield a hydrocarbon product and a first gas stream, wherein the hydrocarbon product comprises $C_5+$ hydrocarbons; (c) optionally introducing at least a portion of the hydrocarbon product to a first aromatics separating unit to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons; (d) feeding at least a portion of the hydrocarbon product and/or at least a portion of the saturated hydrocarbons stream to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the saturated hydrocarbons stream; (e) introducing at least a portion of the reforming unit product to a second aromatics separating unit to produce a non-aromatics recycle stream and a second aromatics stream, wherein the second aromatics stream comprises $C_6+$ aromatic hydrocarbons; (f) recycling at least a portion of the non-aromatics recycle stream to the reforming unit; (g) introducing at least a portion of the first aromatics stream and/or the second aromatics stream to a third aromatics separating unit to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, and wherein the $C_8$ aromatics stream comprises xylenes and ethylbenzene; (h) contacting at least a portion of the $C_7$ aromatics stream, at least a portion of the $C_9$ aromatics stream, at least a portion of the $C_{10}$ aromatics stream, or combinations thereof with a Tatoray catalyst (e.g., disproportionation and transalkylation catalyst) in the presence of hydrogen in a Tatoray unit (e.g., disproportionation and transalkylation unit) to yield a third aromatics stream, wherein the third aromatics stream comprises benzene and xylenes; and (i) conveying at least a portion of the $C_{11}+$ aromatics stream to the mild hydrocracker unit. A process for producing benzene and xylenes as disclosed herein can employ a high severity pyrolysis unit operating at a pyrolysis temperature of equal to or greater than about 450° C. (as opposed to a low severity pyrolysis unit) in conjunction with a downstream mild hydrocracker unit, a reforming unit, and a Tatoray unit, in order to primarily focus production of aromatics to benzene and xylenes; however, a reduced yield of benzene and xylenes is obtained for processes for producing benzene and xylenes employing the high severity pyrolysis unit as compared to otherwise similar processes for producing benzene and xylenes employing the low severity pyrolysis unit. As will be appreciated by one of skill in the art, and with the help of this disclosure, a yield of pyrolysis liquid (e.g., hydrocarbon liquid stream 13) is reduced in a high severity pyrolysis unit (e.g., less than about 50% hydrocarbon liquid product yield) as compared to a low pyrolysis unit, owing to simultaneous high yields of gaseous products (e.g., equal to or greater than about 50%) and light gas olefins (e.g., equal to or greater than about 35%) in the high severity pyrolysis unit.

In some aspects, a system for producing benzene and xylenes can comprise a low severity pyrolysis unit, a mild hydrocracker unit, an optional first aromatics separating unit, a reforming unit, a second aromatics separating unit, a third aromatics separating unit, and a Tatoray unit (e.g., disproportionation and transalkylation unit); wherein the low severity pyrolysis unit is configured to receive a plastic waste and to produce a hydrocarbon liquid stream and a pyrolysis gas stream at a temperature of from about 350° C. to about 450° C.; wherein the mild hydrocracker unit comprises a hydroprocessing catalyst, wherein the mild hydrocracker unit is configured to receive hydrogen and at least a portion of the hydrocarbon liquid stream and to produce a hydrocarbon product and a first gas stream at a temperature of from about 300° C. to about 430° C. and at a pressure of from about 10 barg to about 100 barg, wherein the hydrocarbon product comprises $C_5+$ hydrocarbons, wherein the hydrocarbon product comprises equal to or greater than about 90 wt. % $C_{10}-$ hydrocarbons, based on the total weight of the hydrocarbon product, and wherein the hydrocarbon product comprises less than about 1 wt. % olefins, based on the total weight of the hydrocarbon product; wherein the optional first aromatics separating unit is configured to receive at least a portion of the hydrocarbon product and to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons; wherein the reforming unit comprises a reforming catalyst, wherein the reforming unit is configured to receive at least a portion of the hydrocarbon product and/or at least a portion of the saturated hydrocarbons stream and to produce a reforming unit product, a second gas stream, and a hydrogen stream, wherein an amount of $C_6$ to $C_8$ aromatic hydrocarbons in the reforming unit product is greater than an amount of $C_6$ to $C_8$ aromatic hydrocarbons in the saturated hydrocarbons stream; wherein the second aromatics separating unit is configured to receive at least a portion of the reforming unit product and to produce a non-aromatics recycle stream and a second aromatics stream, and wherein the second aromatics stream comprises $C_6+$ aromatic hydrocarbons; wherein the third aromatics separating unit is configured to receive at least a portion of the first aromatics stream and/or the second aromatics stream and to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, wherein the $C_8$ aromatics stream comprises xylenes and ethylbenzene, and wherein at least a portion of the $C_{11}+$ aromatics stream is recycled to the mild hydrocracker unit; and wherein the Tatoray unit comprises a Tatoray catalyst (e.g., disproportionation and transalkylation catalyst), wherein the Tatoray unit is configured to receive at least a portion of the $C_7$ aromatics stream, at least a portion of the $C_9$ aromatics stream, at least a portion of the $C_{10}$ aromatics stream, or combinations thereof and to produce a third aromatics stream, wherein the third aromatics stream comprises benzene and xylenes, and wherein a $C_9+$ aromatic hydrocarbons content of the combined first $C_6$ aromatics stream, $C_8$ aromatics stream, and third aromatics stream is less than about 5 wt. %, based on the weight of the combined first $C_6$ aromatics stream, $C_8$ aromatics stream, and third aromatics stream.

In other aspects, a system for producing benzene and xylenes can comprise a high severity pyrolysis unit, a mild hydrocracker unit, an optional first aromatics separating unit, a reforming unit, a second aromatics separating unit, a third aromatics separating unit, and a Tatoray unit (e.g., disproportionation and transalkylation unit); wherein the high severity pyrolysis unit is configured to receive a plastic waste and to produce a hydrocarbon liquid stream and a pyrolysis gas stream at a temperature of equal to or greater than about 450° C.; wherein the mild hydrocracker unit comprises a hydroprocessing catalyst, wherein the mild hydrocracker unit is configured to receive hydrogen and at least a portion of the hydrocarbon liquid stream and to produce a hydrocarbon product and a first gas stream at a temperature of from about 300° C. to about 430° C. and at a pressure of from about 10 barg to about 100 barg, wherein the hydrocarbon product comprises $C_5+$ hydrocarbons, wherein the hydrocarbon product comprises equal to or greater than about 90 wt. % $C_{10}-$ hydrocarbons, based on the total weight of the hydrocarbon product, and wherein the hydrocarbon product comprises less than about 1 wt. % olefins, based on the total weight of the hydrocarbon product; wherein the optional first aromatics separating unit is configured to receive at least a portion of the hydrocarbon product and to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons; wherein the reforming unit comprises a reforming catalyst, wherein the reforming unit is configured to receive at least a portion of the hydrocarbon product and/or at least a portion of the saturated hydrocarbons stream and to produce a reforming unit product, a second gas stream, and a hydrogen stream, wherein an amount of $C_6$ to $C_8$ aromatic hydrocarbons in the reforming unit product is greater than an amount of $C_6$ to $C_8$ aromatic hydrocarbons in the saturated hydrocarbons stream; wherein the second aromatics separating unit is configured to receive at least a portion of the reforming unit product and to produce a non-aromatics recycle stream and a second aromatics stream, and wherein the second aromatics stream comprises $C_6+$ aromatic hydrocarbons; wherein the third aromatics separating unit is configured to receive at least a portion of the first aromatics stream and/or the second aromatics stream and to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, wherein the $C_8$ aromatics stream comprises xylenes and ethylbenzene, and wherein at least a portion of the $C_{11}+$ aromatics stream is recycled to the mild hydrocracker unit; and wherein the Tatoray unit comprises a Tatoray catalyst (e.g., disproportionation and transalkylation catalyst), wherein the Tatoray unit is configured to receive at least a portion of the $C_7$ aromatics stream, at least a portion of the $C_9$ aromatics stream, at least a portion of the $C_{10}$ aromatics stream, or combinations thereof and to produce a third aromatics stream, wherein the third aromatics stream comprises benzene and xylenes, and wherein a $C_9+$ aromatic hydrocarbons content of the combined first $C_6$ aromatics stream, $C_8$ aromatics stream, and third aromatics stream is less than about 5 wt. %, based on the weight of the combined first $C_6$ aromatics stream, $C_8$ aromatics stream, and third aromatics stream. As will be appreciated by one of skill in the art, and with the help of this disclosure, a system for producing benzene and xylenes as disclosed herein comprising a low severity pyrolysis unit is characterized by a higher overall benzene and xylenes yield as compared to an otherwise similar system for producing benzene and xylenes comprising a high severity pyrolysis unit, owing to a higher hydrocarbon liquid yield for the low severity pyrolysis unit as compared to a hydrocarbon liquid yield for the high severity pyrolysis unit.

Processes for producing benzene and xylenes as disclosed herein can advantageously display improvements in one or more process characteristics when compared to otherwise similar processes that do not employ recycling of heavy streams (e.g., $C_{11}+$ hydrocarbons). The processes and systems for processing plastic waste as disclosed herein advantageously integrate pyrolysis, hydrocracking, aromatization, and disproportionation and transalkylation to maximize production of mono-ring aromatics in the $C_6$-$C_8$ range, such as benzene and xylenes.

Processes for producing benzene and xylenes as disclosed herein can advantageously consume hydrogen generated in the process, such that no additional or external hydrogen input is required.

Processes for producing benzene and xylenes as disclosed herein advantageously utilize polyolefin-rich feeds to produce high yields of aromatics. Additional advantages of the producing benzene and xylenes as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

Low and high severity pyrolysis of mixed waste plastic were conducted to investigate the production of aromatics. The mixed waste plastic had 82% olefinic feed (e.g., high-density polyethylene (HDPE), low-density polyethylene (LDPE), linear low-density polyethylene (LLDPE), and polypropylene (PP)); 11% polystyrene (PS); and the remaining 7% was polyethylene terephthalate (PET). The pyrolysis was conducted in continuous catalytic/thermal cracking in circulating fluidized bed, as well as in an in-situ fluidized lab scale batch reactor. The data in first column of Table 1 provide low severity catalytic cracking results from the lab scale reactor operated at a catalyst/feed ratio of 6 and an average cup-mix temperature of about 395° C.; while the data in the remaining three columns of Table 1 show catalytic cracking data from a continuously operated circulating fluidized bed pilot unit operated as per the catalyst/feed ratios provided in Table 1. The cracking was done with different compositions of spent fluid catalytic cracking (FCC) catalyst with ZSM-5 based zeolite additive and operated between 390-560° C. cup mix temperature of feed and catalyst. In all cases, the concentration of aromatics in the liquid was greater than 75%, as it can be seen from the data in Table 1. Cracking cup mix temperature was maintained above 390° C. The data in Table 1 demonstrate that it is possible to vary the aromatics yields boiling at less than 240° C. on plastics feed basis from 20 wt. % yield to as high as 36 wt. %, with a corresponding change in yield of light gas olefins.

TABLE 1

| | Catalyst recipe | | | |
|---|---|---|---|---|
| | 62.5% spent FCC catalyst + 37.5% ZSM5 zeolite catalyst Low severity | 80% spent FCC catalyst + 20% ZSM5 zeolite catalyst Low severity | 80% spent FCC catalyst + 20% ZSM5 zeolite catalyst High severity | 65% spent FCC catalyst + 35% ZSM5 zeolite catalyst High severity |
| Avg cup mix temp, ° C. | 394.7 | 452 | 521 | 553.9 |
| Catalyst/Feed, wt./wt. | 6 | 29.4 | 48.5 | 37.2 |
| Plastic feed rate, g/hr | Batch 1.5 g feed | 295 | 282 | 273 |
| Product yields, wt. % | | | | |
| H2-C4 gas | 29.7 | 47.90 | 55.1 | 61.6 |
| Liquids | 65.0 | 43.30 | 35.9 | 31.3 |
| Coke | 5.3 | 8.80 | 6.2 | 5.6 |
| Gasoline | 45.28 | 37.00 | 30.37 | 24.54 |
| Diesel | 17.6 | 5.31 | 4.43 | 5.36 |
| Heavies | 2.1 | 0.99 | 1.06 | 1.41 |
| Total light gas olefins yield, wt. % | 16.55 | 28.55 | 36.61 | 41.65 |
| Total aromatics yield (minus 240° C.), wt. % | 35.6 | 30.61 | 26.07 | 20.61 |
| Aromatics conc. In minus 240° C. cut | 78.58 | 82.74 | 85.84 | 83.97 |

Example 2

The PONA composition (e.g., paraffins, olefins, naphthenes, and aromatic compounds) in Table 2 shows the aromatic concentration from both thermally cracking in a modular low severity cracking unit at ~450° C. and catalytic cracking at an average cup mix temperature of ~452° C. with using a catalyst mixture as outlined in Example 1, in a circulating fluidized bed. The concentration of aromatics varied between 9-90%. The PONA aromatic rich stream when treated further via reforming produced high quantities of $C_6$-$C_9$ high value aromatics.

TABLE 2

| Product composition of mixed plastic pyrolysis after cracking | Thermally cracked from modular technology unit | Catalytically cracked from circulating fluidized bed |
|---|---|---|
| P | 45 | 9.5 |
| O | 34 | 4.2 |
| N | 11 | 3.6 |
| A | 9.4 | 82.7 |

Example 3

Continuous cracking of mixed plastic in circulating fluidized bed reactor was conducted with different combinations of catalyst, and the results of both thermal, as well as catalytic cracking are displayed in Table 3.

TABLE 3

| Cracking type | Catalytic | Catalytic | Catalytic | Thermal | Catalytic | Catalytic |
|---|---|---|---|---|---|---|
| Cup mix temp., ° C. | 556.7 | 551.4 | 550.2 | 550.8 | 552.4 | 452.7 |
| Catalyst/Feed Ratio, wt./wt. | 40 | 41.8 | 43.4 | 33.7 | 28.8 | 29.4 |
| Feed rate, g/hr | 306 | 310 | 265 | 334 | 248 | 295 |
| Catalyst used | 70% Spent FCC catalyst + 30% ZSM-5 zeolite catalyst | 100% FCC spent catalyst with ~3% Rare earth content | 80% Spent FCC Catalyst + 20% ZSM-5 zeolite catalyst | Catalytically Inert material | 100% FCC spent catalyst with ~1% rare earth oxide content | 80% Spent FCC Catalyst + 20% ZSM-5 zeolite catalyst |
| C6 Aromatic content, wt. % | 18.04 | 14.56 | 5.31 | 2.26 | 0.36 | 7.71 |
| C7 Aromatic content, wt. % | 18.23 | 17.14 | 11.94 | 3.41 | 5.25 | 11.38 |
| C8 Aromatic content, wt. % | 25.14 | 29.45 | 31.6 | 26.27 | 35.62 | 30.21 |
| C6-C8 aromatic content, wt. % | 61.41 | 61.15 | 48.85 | 31.94 | 41.23 | 49.3 |
| C9 Aromatic content, wt. % | 10.31 | 8.74 | 17.06 | 3.51 | 21.51 | 16.5 |
| C10 Aromatic content, wt. % | 9.1 | 5.82 | 14.35 | 3.64 | 15.78 | 13.78 |
| C11 Aromatic content, wt. % | 1.54 | 3.08 | 2.26 | 0.76 | 3.38 | 2.29 |
| C12 Aromatic content, wt. % | 0.2 | 0.2 | 0.44 | 0.33 | 0.81 | 0.87 |
| C9-C12 aromatic content, wt. % | 21.15 | 17.84 | 34.11 | 8.24 | 41.48 | 33.44 |
| Liquid product as wt. % of plastic fed | 37.3 | 39.2 | 36 | 67.2 | 30.6 | 43.3 |
| Gasoline cut wt. % (221° C.) in liquid product | 82.91 | 73.36 | 71.58 | 53.96 | 63.82 | 76.8 |
| Diesel cut wt. % (221-370° C.) in liquid product | 15.09 | 19.36 | 26.26 | 25.70 | 31.78 | 20.77 |
| Heavies (370+ ° C.) | 2.00 | 7.27 | 2.16 | 20.34 | 4.40 | 2.43 |
| Gases yield as wt. % of plastic fed | 56.6 | 56.7 | 56.6 | 30.9 | 60.3 | 47.9 |
| H2 | 0.18 | 0.15 | 0.16 | 0.04 | 0.20 | 0.05 |
| CO2 | 1.18 | 1.62 | 1.26 | 1.47 | 0.95 | 1.26 |
| CO | 0.81 | 1.26 | 0.81 | 1.05 | 0.76 | 0.46 |
| CH4 | 0.55 | 0.42 | 0.83 | 0.95 | 1.04 | 0.25 |
| C2H2 | 0 | 0 | 0 | 0 | 0 | 0 |
| C2H6 | 0.9 | 0.75 | 0.99 | 1.26 | 0.97 | 0.48 |
| C2H4 | 8.65 | 9.46 | 7.02 | 2.39 | 5.56 | 3.39 |
| C3H8 | 4.8 | 4.13 | 4.08 | 0.96 | 3.39 | 5.02 |
| C3H6 | 19.29 | 21.71 | 18.78 | 10.89 | 22.23 | 12.93 |
| C4H10 (normal + iso) | 10.81 | 9.36 | 11.73 | 6.32 | 12.87 | 11.83 |
| C4H8 | 9.43 | 7.87 | 10.93 | 5.55 | 12.35 | 12.24 |
| Di-aromatics yield as wt. % of plastic fed | 6 | 5.30 | 6.84 | 10.95 | 8.32 | 7.06 |
| Tri-aromatics yield as wt. % of plastic fed | 2.24 | 1.61 | 2.56 | 3.63 | 2.78 | 2.34 |
| Coke, wt. % | 5.7 | 1.6 | 7.0 | 1.3 | 7.6 | 8.80 |
| Water, wt. % | 0.4 | 2.5 | 0.4 | 0.6 | 1.5 | 0.0 |

The aromatic concentration in a pyrolysis product can be varied between 9 to 87 wt. %, and the concentration of $C_6$-$C_8$ aromatics can be varied between 5-62 wt. %. The $C_{9+}$ aromatics can also be varied between 8-42 wt. %. The concentration of $C_8$ aromatics alone can be greater than 35 wt. %.

Disproportionation and transalkylation of $C_7$, $C_9$ and $C_{10}$ aromatics, mild hydrocracking or dealkylation of alkyl aromatics, or reforming of non-aromatic material can increase the formation of benzene and xylene, as can be seen from data presented in Table 3, following the schematics displayed in FIGS. 1 and 2. The distribution of cracked liquid product in gasoline cut (<221° C.) and Diesel cut ranges (221-370° C.), as well as the $C_6$ to $C_{12}$ aromatic content in gasoline cut is provided in Table 3, for different operating cases.

The liquid products as mentioned in Table 3 (e.g., various liquid fractions in Table 3) could be subjected to mild hydrocracking followed by dealkylation to maximize benzene and xylene yield. The di-aromatics and tri-aromatics could be saturated to provide alkyl mono-aromatics, and such alkyl mono-aromatics could be dealkylated in a mild hydrocracking step. The liquid product from the mild hydrocracking step would have mono-aromatics and non-aromatics, which could be sent "as is" to a downstream reformer, or sent to a downstream reformer after aromatic extraction, as per schematics in FIGS. 1 and 2. The reformer would increase the aromatics yield. Further processing of certain aromatic fractions in a Tatoray unit would increases the benzene and xylene yields. Reforming could be generally carried out in a semi-regenerative fixed bed reformer, or in a continuous catalytic reformer (CCR)-type unit. Pressures of about 18-30 barg and temperatures of about 480-520° C. would be generally employed in semi-regenerative reformers to produce an aromatic reformate.

Example 4

Figure 2A:
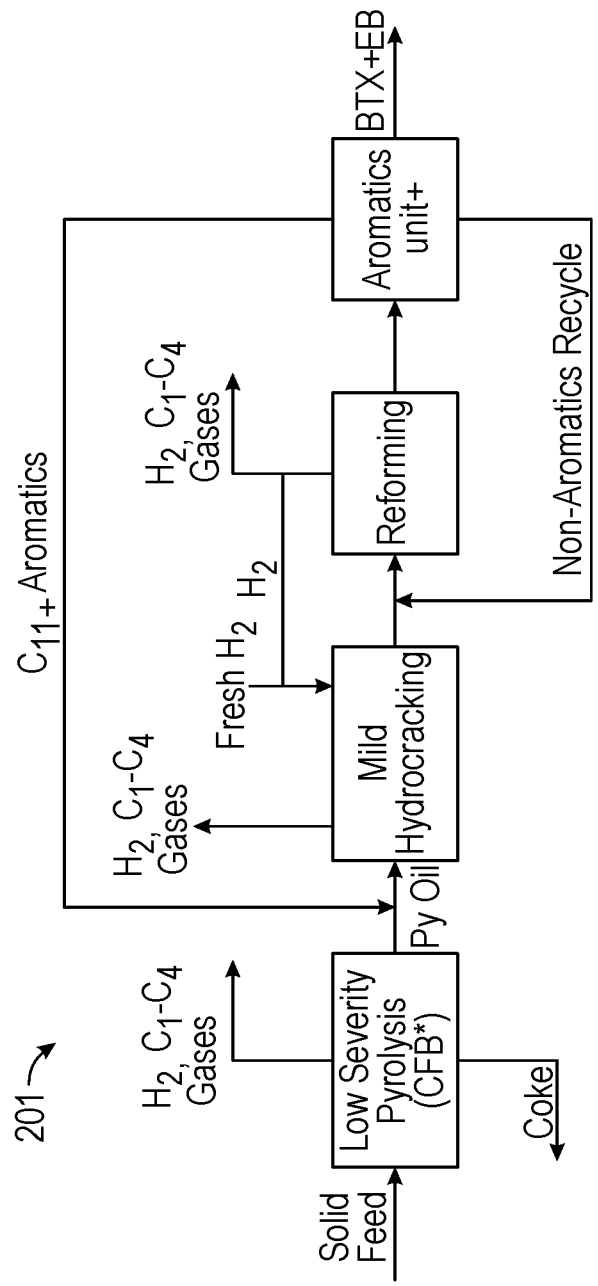
FIG. 2A displays another configuration of a system for producing benzene and xylenes.

A configuration of a system for producing benzene and xylenes 201 is displayed in FIG. 2A. Mixed plastic waste (e.g., solid feed) would be fed to a low severity pyrolyzer in solid form, and then the subsequent liquid product (e.g., py oil or pygas oil) would be hydrocracked in a mild hydrocracker (MHC) to saturate all the liquid olefins and also to reduce the heavies by mild or selective cracking and hydrogenating the liquid and then, the product from the MHC would be sent to a reformer to maximize aromatics. A product stream from the reforming unit would then be sent to an aromatics unit where benzene, toluene, xylene (BTX) and ethylbenzene (EB) would be separated. The aromatics unit could also contain a Tatoray unit, in addition to an aromatics extraction unit, for increasing the yield of benzene and xylenes.

In the case when a plastic feed was processed according to the process schematics displayed in FIGS. 1 and 2, yields at various stages were calculated and are displayed in Table 4. Overall, through the schematic shown in FIG. 2A it is possible to produce about 56 wt. % mono-aromatics (benzene and xylenes, based on mixed plastic fed), in addition to about 19 wt. % of light gas olefins (based on mixed plastic fed). Overall, the high value chemicals produced amount to an yield of about 75 wt. %, based on mixed plastic fed. Hydrogen produced in reforming is not shown in Table 4 for simplification.

TABLE 4

| Compound | After Pyrolysis | After Pyrolysis & MHC | After Reforming | After Tatoray |
| --- | --- | --- | --- | --- |
| Cup mix Temp, ° C. | 550.8 | | | |
| Catalyst | Catalytically inert material in circulating fluid bed | | | |
| C/F ratio, wt./wt. | 33.7 | | | |
| Feed rate, g/hr | 334 | | | |
| Hydrogen | 0.04 | 0.04 | 0.04 | 0.04 |
| Methane | 0.95 | 0.95 | 1.00 | 1.26 |
| Acetylene | 0 | 0.00 | 0.00 | 0.00 |
| Ethylene | 2.39 | 2.39 | 2.39 | 2.39 |
| Ethane | 1.26 | 1.26 | 2.51 | 2.51 |
| Methylacetylene and Propadiene (MAPD) | 0 | 0.00 | 0.00 | 0.00 |
| Propylene | 10.89 | 10.89 | 10.89 | 10.89 |
| Propane | 0.96 | 1.45 | 6.77 | 6.77 |
| Butadiene | 0 | 0.00 | 0.00 | 0.00 |
| Butylene | 5.55 | 5.55 | 5.55 | 5.55 |
| Butanes | 6.32 | 6.93 | 10.08 | 10.08 |
| CO | 1.05 | 1.05 | 1.05 | 1.05 |
| CO2 | 1.47 | 1.47 | 1.47 | 1.47 |
| Gases | 30.88 | 31.98 | 41.75 | 42.01 |
| Liquid product, wt. % | 67.2 | 66.10 | 56.34 | 56.13 |
| Gasoline, wt. % | 36.26 | | | |
| Diesel, wt. % | 17.27 | | | |
| Heavies, wt. % | 13.67 | | | |

TABLE 4-continued

| Compound | After Pyrolysis | After Pyrolysis & MHC | After Reforming | After Tatoray |
| --- | --- | --- | --- | --- |
| Mono-aromatics, wt. % | 39.89 | 29.54 | 55.87 | 55.66 |
| Benzene, wt. % | 0.90 | 17.70 | 19.62 | 23.05 |
| Toluene, wt. % | 1.36 | 1.36 | 10.98 | |
| C8 aromatics, wt. % | 10.48 | 10.48 | 22.64 | 32.38 |
| C9 aromatics, wt. % | 1.40 | 0.00 | 2.63 | |
| C10 aromatics, wt. % | 1.45 | 0.00 | | 0.23 |
| C11 aromatics, wt. % | 0.30 | 0.00 | | |
| C12 aromatics, wt. % | 0.13 | 0.00 | | |
| C13+ monoaromatics, wt. % | 23.86 | | | |
| Di-aromatics, wt. % | 10.95 | | | |
| Tri-aromatics, wt. % | 3.63 | | | |
| Liquid Non-aromatics, wt. % | 12.73 | 36.56 | 0.47 | 0.47 |
| Coke | 1.3 | 1.3 | 1.3 | 1.3 |
| Water | 0.62 | 0.62 | 0.62 | 0.62 |

Figure 2B:
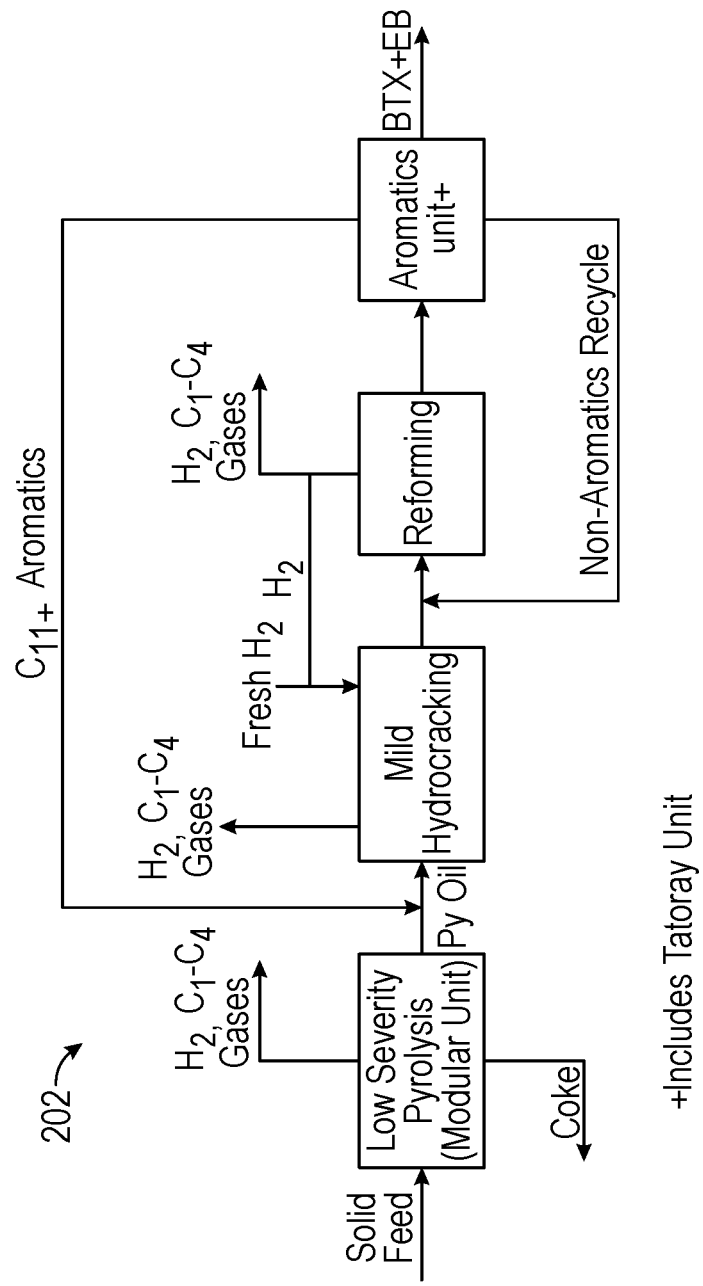
FIG. 2B displays yet another configuration of a system for producing benzene and xylenes.

A configuration of a system for producing benzene and xylenes 202 is displayed in FIG. 2B, wherein mixed plastic waste (e.g., solid feed) would be pyrolyzed in a modular unit (MU) with a liquid product (e.g., py oil or pygas oil) yield of 80 wt. % based on plastic feed, a gas yield of 15 wt. %, and a coke yield of 5 wt. %. Since the liquid product yield from the pyrolysis MU (about 80 wt. %) in system 202 is higher than the liquid product yield from the circulating fluid bed pyrolyzer (about 67 wt. %) in system 201, it would possible to get higher yields of aromatics (about 60 wt. % or higher) with system 202 as compared to system 201. System 202 would produce lower yields of product gases and light gas olefins as compared to system 201. In system 202, the hydrogen produced during reforming would be internally consumed in the MHC.

The overall combination of both high and low severity pyrolysis, followed by mild hydrocracking and reforming, with toluene conversion and heavies' conversion would produce benzene yields of greater than 20% and xylenes yields of greater than 30%.

The present disclosure is further illustrated by the following embodiments, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

Additional Disclosure

The following are enumerated embodiments which are provided as non-limiting examples.

A first aspect, which is a process for producing benzene and xylenes comprising (a) contacting a hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons; (b) optionally introducing at least a portion of the hydrocarbon product to a first aromatics separating unit to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons; (c) feeding at least a portion of the hydrocarbon product and/or at least a portion of the saturated hydrocarbons stream to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the saturated hydrocarbons stream; (d) introducing at least a portion of the reforming unit product to a second aromatics separating unit to produce a non-aromatics recycle stream and a second aromatics stream, wherein the second aromatics stream comprises $C_6+$ aromatic hydrocarbons; (e) recycling at least a portion of the non-aromatics recycle stream to the reforming unit; (f) introducing at least a portion of the first aromatics stream and/or the second aromatics stream to a third aromatics separating unit to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, and wherein the $C_8$ aromatics stream comprises xylenes and ethylbenzene; (g) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes; and (h) conveying at least a portion of the $C_{11}+$ aromatics stream to the hydroprocessing unit.

A second aspect, which is the process of the first aspect, wherein the hydrocarbon liquid stream comprises a plastic pyrolysis oil and/or a tire pyrolysis oil.

A third aspect, which is the process of any one of the first and the second aspects further comprising converting a plastic waste to the hydrocarbon liquid stream and a pyrolysis gas stream in a pyrolysis unit.

A fourth aspect, which is the process of the third aspect further comprising conveying at least a portion of the $C_{11}+$ aromatics stream to the pyrolysis unit.

A fifth aspect, which is the process of any one of the first through the fourth aspects, wherein the pyrolysis gas stream, the first gas stream, the second gas stream, or combinations thereof comprise $H_2$ and $C_1$ to $C_4$ hydrocarbons.

A sixth aspect, which is the process of any one of the first through the fifth aspects, wherein the pyrolysis gas stream, the first gas stream, the second gas stream, or combinations thereof are used as a fuel in the reforming unit, the pyrolysis unit, the hydroprocessing unit, or combinations thereof.

A seventh aspect, which is the process of any one of the first through the sixth aspects, wherein the plastic waste comprises polyolefins, polyethylene, polypropylene, polystyrene, polyvinylchloride (PVC), polyvinylidene chloride (PVDC), or combinations thereof.

An eighth aspect, which is the process of any one of the first through the seventh aspects further comprising recycling at least a portion of the hydrogen stream to the hydroprocessing unit.

A ninth aspect, which is the process of any one of the first through the eighth aspects, wherein the hydroprocessing catalyst comprises cobalt and molybdenum on an alumina support, nickel and molybdenum on an alumina support, tungsten and molybdenum on an alumina support, cobalt and molybdenum oxides on an alumina support, nickel and molybdenum oxides on an alumina support, tungsten and molybdenum oxides on an alumina support, cobalt and molybdenum sulphides on an alumina support, nickel and molybdenum sulphides on an alumina support, tungsten and molybdenum sulphides on an alumina support, a zeolite comprising one or more metals, or combinations thereof.

A tenth aspect, which is the process of the ninth aspect, wherein each metal of the one or more metals can be selected from the group consisting of cobalt, molybdenum, tungsten, nickel, titanium, copper, magnesium, tin, iron, zinc, tungsten, vanadium, gallium, calcium, manganese, ruthenium and rhenium; and wherein the zeolite comprises ZSM-5, ZSM-11, Y, high-silica Y, USY, or combinations thereof.

An eleventh aspect, which is the process of any one of the first through the tenth aspects, wherein the step (a) of contacting a hydrocarbon liquid stream with a hydroprocessing catalyst is performed at a temperature of from about 250° C. to about 600° C.

A twelfth aspect, which is the process of any one of the first through the eleventh aspects, wherein the step (a) of contacting a hydrocarbon liquid stream with a hydroprocessing catalyst is performed at a pressure of from about 1 barg to about 200 barg.

A thirteenth aspect, which is the process of any one of the first through the twelfth aspects, wherein the hydroprocessing unit comprises a mild hydrocracking unit.

A fourteenth aspect, which is the process of the thirteenth aspect, wherein the hydroprocessing unit further comprises a hydrodealkylating unit, and wherein the hydrodealkylating unit comprises a hydrodealkylating catalyst.

A fifteenth aspect, which is the process of any one of the first through the fourteenth aspects, wherein the hydrocarbon product comprises equal to or greater than about 90 wt. % $C_{10}-$ hydrocarbons, based on the total weight of the hydrocarbon product.

A sixteenth aspect, which is the process of any one of the first through the fifteenth aspects, wherein the hydrocarbon product comprises less than about 1 wt. % olefins, based on the total weight of the hydrocarbon product.

A seventeenth aspect, which is the process of any one of the first through the sixteenth aspects further comprising separating the $C_8$ aromatics stream into a first xylenes stream and an ethylbenzene stream.

An eighteenth aspect, which is the process of the seventeenth aspect further comprising conveying at least a portion of the ethylbenzene stream to the disproportionation and transalkylation unit.

A nineteenth aspect, which is the process of any one of the first through the eighteenth aspects further comprising isomerizing at least a portion of the ethylbenzene stream to produce xylenes in an isomerizing unit, wherein the isomerizing unit comprises an isomerization catalyst.

A twentieth aspect, which is the process of any one of the first through the nineteenth aspects further comprising dealkylating at least a portion of the ethylbenzene stream to produce benzene in a dealkylation unit, wherein the dealkylation unit comprises a dealkylation catalyst.

A twenty-first aspect, which is the process of any one of the first through the twentieth aspects, wherein the disproportionation and transalkylation catalyst comprises a zeolite; a ZSM-5 characterized by Si/Al ratio of equal to or greater than about 15:1; a metal loaded ZSM-5, wherein the metal comprises platinum, molybdenum, magnesium, rhenium, or combinations thereof; mordenite; a bismuth oxide loaded mordenite; beta zeolite; MCM-22; or combinations thereof.

A twenty-second aspect, which is the process of any one of the first through the twenty-first aspects, wherein a $C_9+$ aromatic hydrocarbons content of the combined first $C_6$ aromatics stream, $C_8$ aromatics stream, and third aromatics stream is less than about 5 wt. %, based on the weight of the combined first $C_6$ aromatics stream, $C_8$ aromatics stream, and third aromatics stream.

A twenty-third aspect, which is the process of any one of the first through the twenty-second aspects, wherein an overall benzene and xylenes yield is equal to or greater than about 40%.

A twenty-fourth aspect, which is the process of any one of the first through the twenty-third aspects, wherein an overall benzene yield is equal to or greater than about 18 wt. %.

A twenty-fifth aspect, which is the process of any one of the first through the twenty-fourth aspects, wherein an overall xylenes yield is equal to or greater than about 20 wt. %.

A twenty-sixth aspect, which is the process of any one of the first through the twenty-fifth aspects, wherein an overall xylenes yield is equal to or greater than about 30 wt. %.

A twenty-seventh aspect, which is the process of any one of the first through the twenty-sixth aspects further comprising conveying at least a portion of the hydrogen stream to the disproportionation and transalkylation unit.

A twenty-eighth aspect, which is the process of any one of the first through the twenty-seventh aspects further comprising separating the third aromatics stream into a second $C_6$ aromatics stream comprising benzene and a second xylenes stream.

A twenty-ninth aspect, which is a process for producing benzene and xylenes comprising (a) converting a plastic waste to a hydrocarbon liquid stream and a pyrolysis gas stream in a pyrolysis unit; (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons; (c) optionally introducing at least a portion of the hydrocarbon product to a first aromatics separating unit to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons; (d) feeding at least a portion of the hydrocarbon product and/or at least a portion of the saturated hydrocarbons stream to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the saturated hydrocarbons stream; (e) introducing at least a portion of the reforming unit product to a second aromatics separating unit to produce a non-aromatics recycle stream and a second aromatics stream, wherein the second aromatics stream comprises $C_6+$ aromatic hydrocarbons; (f) recycling at least a portion of the non-aromatics recycle stream to the reforming unit; (g) introducing at least a portion of the first aromatics stream and/or the second aromatics stream to a third aromatics separating unit to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, and wherein the $C_8$ aromatics stream comprises xylenes and ethylbenzene; (h) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes; and (i) conveying at least a portion of the $C_{11}+$ aromatics stream to the hydroprocessing unit.

A thirtieth aspect, which is a system for producing benzene and xylenes comprising a pyrolysis unit, a hydroprocessing unit, an optional first aromatics separating unit, a reforming unit, a second aromatics separating unit, a third aromatics separating unit, and a disproportionation and transalkylation unit; wherein the pyrolysis unit is configured to receive a plastic waste and to produce a hydrocarbon liquid stream and a pyrolysis gas stream; wherein the hydroprocessing unit comprises a hydroprocessing catalyst, wherein the hydroprocessing unit is configured to receive hydrogen and at least a portion of the hydrocarbon liquid stream and to produce a hydrocarbon product and a first gas stream, wherein the hydrocarbon product comprises $C_5+$ hydrocarbons, wherein the hydrocarbon product comprises equal to or greater than about 90 wt. % $C_{10}-$ hydrocarbons, based on the total weight of the hydrocarbon product, and wherein the hydrocarbon product comprises less than about 1 wt. % olefins, based on the total weight of the hydrocarbon product; wherein the optional first aromatics separating unit is configured to receive at least a portion of the hydrocarbon product and to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons; wherein the reforming unit comprises a reforming catalyst, wherein the reforming unit is configured to receive at least a portion of the hydrocarbon product and/or at least a portion of the saturated hydrocarbons stream and to produce a reforming unit product, a second gas stream, and a hydrogen stream, wherein an amount of $C_6$ to $C_8$ aromatic hydrocarbons in the reforming unit product is greater than an amount of $C_6$ to $C_8$ aromatic hydrocarbons in the saturated hydrocarbons stream; wherein the second aromatics separating unit is configured to receive at least a portion of the reforming unit product and to produce a non-aromatics recycle stream and a second aromatics stream, and wherein the second aromatics stream comprises $C_6+$ aromatic hydrocarbons; wherein the third aromatics separating unit is configured to receive at least a portion of the first aromatics stream and/or the second aromatics stream and to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, wherein the $C_8$ aromatics stream comprises xylenes and ethylbenzene, and wherein at least a portion of the $C_{11}+$ aromatics stream is recycled to the hydroprocessing unit; and wherein the disproportionation and transalkylation unit comprises a disproportionation and transalkylation catalyst, wherein the disproportionation and transalkylation unit is configured to receive at least a portion of the $C_7$ aromatics stream, at least a portion of the $C_9$ aromatics stream, at least a portion of the $C_{10}$ aromatics stream, or combinations thereof and to produce a third aromatics stream, wherein the third aromatics stream comprises benzene and xylenes, and wherein a $C_9+$ aromatic hydrocarbons content of the combined first $C_6$ aromatics stream, $C_8$ aromatics stream, and third aromatics stream is less than about 5 wt. %, based on the weight of the combined first $C_6$ aromatics stream, $C_8$ aromatics stream, and third aromatics stream.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing benzene and xylenes comprising:
    (a) contacting a hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons;
    (b) optionally introducing at least a portion of the hydrocarbon product to a first aromatics separating unit to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons;
    (c) feeding at least a portion of the hydrocarbon product and/or at least a portion of the saturated hydrocarbons stream to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the saturated hydrocarbons stream;
    (d) introducing at least a portion of the reforming unit product to a second aromatics separating unit to produce a non-aromatics recycle stream and a second aromatics stream, wherein the second aromatics stream comprises $C_6+$ aromatic hydrocarbons;
    (e) recycling at least a portion of the non-aromatics recycle stream to the reforming unit;
    (f) introducing at least a portion of the first aromatics stream and/or the second aromatics stream to a third aromatics separating unit to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, and wherein the $C_8$ aromatics stream comprises xylenes and ethylbenzene;
    (g) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes; and
    (h) conveying at least a portion of the $C_{11}+$ aromatics stream to the hydroprocessing unit.

2. The process of claim 1, further comprising converting a plastic waste to the hydrocarbon liquid stream and a pyrolysis gas stream in a pyrolysis unit.

3. The process of claim 2, further comprising conveying at least a portion of the $C_{11}+$ aromatics stream to the pyrolysis unit.

4. The process of claim 1, further comprising converting a plastic waste to the hydrocarbon liquid stream and a pyrolysis gas stream in a pyrolysis unit, wherein the pyrolysis gas stream, the first gas stream, the second gas stream, or combinations thereof comprise $H_2$ and $C_1$ to $C_4$ hydrocarbons.

5. The process of claim 1, further comprising recycling at least a portion of the hydrogen stream to the hydroprocessing unit.

6. The process of claim 1, wherein the step (a) of contacting a hydrocarbon liquid stream with a hydroprocessing catalyst is performed at a temperature of from about 250° C. to about 600° C., and at a pressure of from about 1 barg to about 200 barg.

7. The process of claim 1, wherein the hydroprocessing unit comprises a mild hydrocracking unit.

8. The process of claim 1, wherein the hydrocarbon product comprises equal to or greater than about 90 wt. % $C_{10}-$ hydrocarbons, based on the total weight of the hydrocarbon product.

9. The process of claim 1, wherein the hydrocarbon product comprises less than about 1 wt. % olefins, based on the total weight of the hydrocarbon product.

10. The process of claim 1, further comprising separating the $C_8$ aromatics stream into a first xylenes stream and an ethylbenzene stream.

11. The process of claim 10, further comprising conveying at least a portion of the ethylbenzene stream to the disproportionation and transalkylation unit.

12. The process of claim 1, further comprising (i) isomerizing at least a portion of the ethylbenzene stream to produce xylenes in an isomerizing unit, wherein the isomerizing unit comprises an isomerization catalyst; and/or (ii) dealkylating at least a portion of the ethylbenzene stream to produce benzene in a dealkylation unit, wherein the dealkylation unit comprises a dealkylation catalyst.

13. The process of claim 1, wherein a $C_9+$ aromatic hydrocarbons content of the combined first $C_6$ aromatics stream, $C_8$ aromatics stream, and third aromatics stream is less than about 5 wt. %, based on the weight of the combined first $C_6$ aromatics stream, $C_8$ aromatics stream, and third aromatics stream.

14. The process of claim 1, wherein an overall benzene and xylenes yield is equal to or greater than about 40 wt. %.

15. The process of claim 1, wherein an overall benzene yield is equal to or greater than about 18 wt. %.

16. The process of claim 1, wherein an overall xylenes yield is equal to or greater than about 20 wt. %.

17. The process of claim 1, further comprising separating the third aromatics stream into a second $C_6$ aromatics stream comprising benzene and a second xylenes stream.

18. A process for producing benzene and xylenes comprising:
    (a) contacting a hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons;
    (b) optionally introducing at least a portion of the hydrocarbon product to a first aromatics separating unit to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons;

(c) feeding at least a portion of the hydrocarbon product and/or at least a portion of the saturated hydrocarbons stream to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the saturated hydrocarbons stream;

(d) introducing at least a portion of the reforming unit product to a second aromatics separating unit to produce a non-aromatics recycle stream and a second aromatics stream, wherein the second aromatics stream comprises $C_6+$ aromatic hydrocarbons;

(e) recycling at least a portion of the non-aromatics recycle stream to the reforming unit;

(f) introducing at least a portion of the first aromatics stream and/or the second aromatics stream to a third aromatics separating unit to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, and wherein the $C_8$ aromatics stream comprises xylenes and ethylbenzene;

(g) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes; and (h) conveying at least a portion of the $C_{11}+$ aromatics stream to the hydroprocessing unit, further comprising converting a plastic waste to the hydrocarbon liquid stream and a pyrolysis gas stream in a pyrolysis unit, wherein the pyrolysis gas stream, the first gas stream, the second gas stream, or combinations thereof are used as a fuel in the reforming unit, the pyrolysis unit, the hydroprocessing unit, or combinations thereof.

19. A system for producing benzene and xylenes comprising a pyrolysis unit, a hydroprocessing unit, an optional first aromatics separating unit, a reforming unit, a second aromatics separating unit, a third aromatics separating unit, and a disproportionation and transalkylation unit;

wherein the pyrolysis unit is configured to receive a plastic waste and to produce a hydrocarbon liquid stream and a pyrolysis gas stream;

wherein the hydroprocessing unit comprises a hydroprocessing catalyst, wherein the hydroprocessing unit is configured to receive hydrogen and at least a portion of the hydrocarbon liquid stream and to produce a hydrocarbon product and a first gas stream, wherein the hydrocarbon product comprises $C_5+$ hydrocarbons, wherein the hydrocarbon product comprises equal to or greater than about 90 wt. % $C_{10}-$ hydrocarbons, based on the total weight of the hydrocarbon product, and wherein the hydrocarbon product comprises less than about 1 wt. % olefins, based on the total weight of the hydrocarbon product;

wherein the optional first aromatics separating unit is configured to receive at least a portion of the hydrocarbon product and to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons;

wherein the reforming unit comprises a reforming catalyst, wherein the reforming unit is configured to receive at least a portion of the hydrocarbon product and/or at least a portion of the saturated hydrocarbons stream and to produce a reforming unit product, a second gas stream, and a hydrogen stream, wherein an amount of $C_6$ to $C_8$ aromatic hydrocarbons in the reforming unit product is greater than an amount of $C_6$ to $C_8$ aromatic hydrocarbons in the saturated hydrocarbons stream;

wherein the second aromatics separating unit is configured to receive at least a portion of the reforming unit product and to produce a non-aromatics recycle stream and a second aromatics stream, and wherein the second aromatics stream comprises $C_6+$ aromatic hydrocarbons;

wherein the third aromatics separating unit is configured to receive at least a portion of the first aromatics stream and/or the second aromatics stream and to produce a first $C_6$ aromatics stream, a $C_7$ aromatics stream, a $C_8$ aromatics stream, a $C_9$ aromatics stream, a $C_{10}$ aromatics stream, and a $C_{11}+$ aromatics stream, wherein the first $C_6$ aromatics stream comprises benzene, wherein the $C_7$ aromatics stream comprises toluene, wherein the $C_8$ aromatics stream comprises xylenes and ethylbenzene, and wherein at least a portion of the $C_{11}+$ aromatics stream is recycled to the hydroprocessing unit; and wherein the disproportionation and transalkylation unit comprises a disproportionation and transalkylation catalyst, wherein the disproportionation and transalkylation unit is configured to receive at least a portion of the $C_7$ aromatics stream, at least a portion of the $C_9$ aromatics stream, at least a portion of the $C_{10}$ aromatics stream, or combinations thereof and to produce a third aromatics stream, wherein the third aromatics stream comprises benzene and xylenes, and wherein a $C_9+$ aromatic hydrocarbons content of the combined first $C_6$ aromatics stream, $C_8$ aromatics stream, and third aromatics stream is less than about 5 wt. %, based on the weight of the combined first $C_6$ aromatics stream, $C_8$ aromatics stream, and third aromatics stream.

* * * * *